(12) United States Patent
Puymirat et al.

(10) Patent No.: US 8,546,077 B2
(45) Date of Patent: Oct. 1, 2013

(54) PROSTAGLANDIN E2 MODULATION AND USES THEREOF

(75) Inventors: Jack Puymirat, Quebec (CA); Daniel Beaulieu, Quebec (CA); Pierre Chapdelaine, Saint-Romuald (CA)

(73) Assignee: Université Laval, Quebec (CA)

( * ) Notice: Subject to any disclaimer, the term of this patent is extended or adjusted under 35 U.S.C. 154(b) by 317 days.

(21) Appl. No.: 12/816,820

(22) Filed: Jun. 16, 2010

(65) Prior Publication Data

US 2010/0304416 A1    Dec. 2, 2010

Related U.S. Application Data

(62) Division of application No. 12/205,194, filed on Sep. 5, 2008, now abandoned.

(60) Provisional application No. 60/971,392, filed on Sep. 11, 2007.

(51) Int. Cl.
| | |
|---|---|
| C12Q 1/68 | (2006.01) |
| C12N 5/00 | (2006.01) |
| C12N 5/02 | (2006.01) |
| A61K 49/00 | (2006.01) |
| C07H 21/04 | (2006.01) |

(52) U.S. Cl.
CPC .................................. C12Q 1/6883 (2013.01)
USPC ............. 435/6.1; 424/9.1; 435/375; 435/377; 536/24.5

(58) Field of Classification Search
None
See application file for complete search history.

(56) References Cited

U.S. PATENT DOCUMENTS

| | | | |
|---|---|---|---|
| 7,192,733 B2 | 3/2007 | Jakobsson et al. | |
| 7,273,883 B2 | 9/2007 | Woodward et al. | |
| 2002/0169209 A1* | 11/2002 | Horrobin | 514/560 |
| 2005/0059742 A1 | 3/2005 | Jabbour et al. | |
| 2006/0135490 A1 | 6/2006 | Fitzgerald et al. | |
| 2007/0054259 A1 | 3/2007 | Kim et al. | |
| 2007/0099857 A1 | 5/2007 | Blomqvist et al. | |
| 2007/0142638 A1 | 6/2007 | Hattori et al. | |
| 2007/0208017 A1 | 9/2007 | Chau et al. | |
| 2007/0225217 A1 | 9/2007 | Chappell et al. | |
| 2008/0248501 A1* | 10/2008 | LePage et al. | 435/7.23 |

FOREIGN PATENT DOCUMENTS

| | | |
|---|---|---|
| EP | 0776663 | 6/1997 |
| EP | 1328621 | 7/2003 |
| NZ | 513172 | 10/2003 |
| WO | WO97/18811 | 4/1997 |
| WO | WO00/16760 | 3/2000 |
| WO | WO00/18744 | 3/2000 |
| WO | WO 2005053601 A2 * | 6/2005 |

OTHER PUBLICATIONS

Ho et al., Transgenic mice expression CUG-BP1 reproduce splicing mis-regulation observed in myotonic dystrophy, 2005, Human Molecular Genetics, vol. 14, pp. 1539-1547.*

Cheng et al., Cyclooxygenases, microsomal prostaglandin E synthase-1, and cardiovascular function, 2006, The Journal of Clinical Investigation, vol. 116, pp. 1391-1399.*

Schutzle, U.B., Wakelam, and D. Pette, Prostaglandins and cyclic AMP stimulate creatine kinase synthesis but not fusion in cultured embryonic chick muscle cells. Biochim Biophys Acta, 1984.805(2): p. 204-10.

Zalin, R.J., Prostaglandins and myoblast fusion. Dev Biol, 1977. 59(2): p. 241-8.

David, J.D. and C.A. Higginbotham, Fusion of chick embryo skeletal myoblasts: interactions of prostaglandin E1, adenosine 3':5' monophosphate, and calcium influx. Dev Biol; 1981. 82(2): p. 308-16.

Entwistle, A., D.H. Curtis, and R.J. Zalin, Myoblast fusion is regulated by a prostanoid of the one series independently of a rise in cyclic AMP. J Cell Biol, 1986. 103(3): p. 857-66.

Rossi, M.J., M.A. Clark, and S.M. Steiner, Possible role of prostaglandins in the regulation of mouse myoblasts. J Cell. Physiol, 1989. 141(1): p. 142-7.

Templeton, G.H., M. Padalino, and R. Moss, Influences of inactivity and indomethacin on soleus phosphatidylethanolamine and size. Prostaglandins, 1986. 31(3): p. 545-59.

McLennan, I.S., Characterization of a prostaglandin dysfunction myopathy. Muscle Nerve, 1987. 10(9): p. 801-9.

McLennan, I.S., Hormonal regulation of myoblast proliferation and myotube production in vivo: influence of prostaglandins. JExp Zool, 1987, 241(2): p. 237-45.

Shen, W., et al., Inhibited skeletal muscle healing in cyclooxygenase-2 gene-deficient mice: the role of PGE2 and PGF2alpha. J Appl Physiol, 2006. 101(4): p. 1215-21.

Horrobin, D.F., et al., The roles of prostaglandins and calcium accumulation in muscular dystrophy. Med Hypotheses, 1977. 3(4): p. 150-3.

Mahadevan et al., Myotonic dystrophhy mutation: an unstable CTG repeat in the 3' untranslated region of the gene, 1992. Science 255:1253-1255.

Fu et al., An unstable triplet repeat in a gene related to myotonic muscular dystrophy, 1992. Science 255:1256-1258.

Brook et al., Molecular basis of myotonic dystrophy: expansion of a trinucleotide (CTG) repeat at the 3' end of a transcript encoding a protein kinase family member, 1992. Cell 68:799-808.

Furling et al., Changes in myotonic dystrophy protein kinease levels and muscle development in congenital myotonic dystrophy, 2003. Am J Pathol. 162:1001-1009.

Tsilfidis et al., Correlation between CTG trinucleotide repeat length and frequency of severe congenital myotonic dystrophy, 1992. Nat Genet 1:192-195.

Hunter et al., The correlation of age of onset with CTG trinucleotide repeat amplification in myotonic dystrophy, 1992. J Med Genet 29:774-779.

(Continued)

Primary Examiner — Dana Shin

(74) Attorney, Agent, or Firm — Goudreau Gage Dubuc; S. Serge Shahinian; Alain Dumont

(57) ABSTRACT

Methods, uses, kits and products are described for the prognosis, diagnosis, prevention and treatment of myotronic dystrophy type 1 (DM1), and more particularly for the prognosis, diagnosis, prevention and treatment of the congenital form of myotronic dystrophy type 1 (cDM1), based on changes in/modulation of prostaglandin $E_2$ (PGE$_2$).

8 Claims, 19 Drawing Sheets

(56) References Cited

OTHER PUBLICATIONS

Murakami et al., Recent advances in molecular biology and physiology of the prostaglandin E2-biosynthetic pathway, 2004. Progress in Lipid Research 43: 3-35.
Portanova et al., Selective Neutralization of Prostaglandin E2 blocks inflammation, hyperalgesia, and interleukin 6 production in vivo, 1996. J. Exp. Med. 184: 883-91.
Langlois et al., Hammerhead robozyme-mediated destruction of nuclear foci in myotonic dystrophy myoblasts, 2003 Mol. Ther. 7: 670-680.
Furling D et al., Decreased levels of myotonic dystrophy protein kinase (DMPK) and delayed differentiation in human myotonic dystrophy myoblasts, 2001. Neuromuscul Disord. 11: 728-35.
Gross-Bellard et al., Isolation of high-molecular-weight DNA from mammalian cells, 1973. Eur J Biochem 36: 32-38.
Chapdelaine et al., Decidualization and maintenance of a functional prostaglandin system in human endometrial cell lines following transformation with SV40 large T antigen, 2006. Mol. Hum. Reprod. 12: 309-319.
Asselin et al., Influence of sex steroids on the production of prostaglandins F2a and E2 and response to oxytocin in cultured epithelial and stromal cells of the bovine endometrium, 1996. Biol. Reprod. 54: 371-379.
Steinbach et al., The DMPK gene of severely affected myotonic dystrophy patients is hypermethylated proximal to the largely expanded CTG repeat, 1998. Am J Hum Genet. 62(2): 278-85.
Filippova et al., CTCF-binding sites flank CTG/CAG repeats and form a methylation-sensitive insulator at the DM1 locus, 2001. Nat Genet. 28(4): 335-43.
Vane and Botting, The mechanism of action of aspirin, 2003. Thromb Res. 110: 255-258.
Prisk and Huard, Muscle injuries and repair: the role of prostaglandins and inflammation, Histol Histopathol (2003) 18: 1243-1256.
Horsley, V. and G.K. Pavlath, Prostaglandin F2(alpha) stimulates growth of skeletal muscle cells via an NFATC2-dependent pathway. J. Cell Biol., 2003. 161(1): p. 111-118.
Amack, J.D. et al., "Mutant DMPK 3'-UTR transcripts disrupt C2C12 myogenic differentiation by compromising MyoD", The Journal of Cell Biology, 159:3:419-429 (2002).
Blau, H.M. et al. "Differentiation properties of pure populations of human dystrophic muscle cells", Exp Cell Res, 144:495-503 (1983).
Buas, M.F. et al., "Inhibition of myogenesis by notch: evidence of multiple pathways", J. Cell. Physiol., 218:84-93 (2009).
Chen et al., "microRNA-1 and microRNA-206 regulate skeletal muscle satellite cell proliferation and differentiation by repressing Pax7", J. Cell. Biol., 190:5:867-879 (2010).

Friedrichs, M. et al., "BMP signaling balances proliferation and differentiation of muscle satellite cell descendants", BMC Cell Biology, 12:26:1471-2121 (2011).
Jackson, M.J. et al., "Creatine kinase and prostaglandin E2 release from isolated Duchenne muscle", Neurology, 41:101-104 (1991).
Perbellini, R. et al. "Dysregulation and cellular mislocalization of specific miRNAs in myotonic dystrophy type 1", Neuromuscular Disorders, 21:81-88 (2011).
Shen et al., "The Notch coactivator, MAML1, functions as a novel coactivator for MEF2C-mediated transcription and is required for normal myogenesis", Genes Dev., 20:675-688 (2006).
Shi et al., "BMP antagonists enhance myogenic differentiation and ameliorate the dystrophic phenotype in a DMD mouse model", Neurobiology of Disease, 41:353-360 (2011).
Spangenburg, E. E., "SOCS-3 induces myoblast differentiations", The Journal of Biological Chemistry, 280:11:10749-10758 (2005).
Timchenko, N. A. et al., "Overexpression of CUG triplet repeat-binding protein, CUGBP1, in mice inhibits myogenesis", The Journal of Biological Chemistry, 279:13:13129-13139 (2004).
Wu et al., "p38 and extracellular signal-regulated kinases regulate the myogenic program at multiple steps", Mol. Cell. Biol., 20:11:3951-3964 (2000).
Zalin, R.J., "Prostaglandins and myoblast fusion", Developmental Biology, 59:241-248 (1977).
Schara, U. and B.G. Schoser, Myotonic dystrophies type 1 and 2: a summary on current aspects. Semin Pediatr Neural, 2006. 13(2): p. 71-9.
Wheeler, T.M. and C.A. Thornton, Myotonic dystrophy: RNA-mediated muscle disease. Curr Opin Neurol, 2007. 20(5): p. 572-6.
Amack, J.D. and M.S. Mahadevan, Myogenic defects in myotonic dystrophy. Dev Biol, 2004. 265(2): p. 294-301.
Martinez-Gonzalez, J. and L. Badimon, Mechanisms underlying the cardiovascular effects of COX-inhibition: benefits and risks. Curr Pharm Des, 2007. 13(22): p. 2215-27.
Davies, N. M., et al., Cyclooxygenase-3: axiom, dogma, anomaly, enigma or splice error?—Not as easy as 1, 2, 3. J Pharm Pharm Sci, 2004. 7(2): p. 217-26.
Mattia, C. and F. Coluzzi, COX-2 inhibitors: pharmacological data and adverse effects. Minerva Anestesiol, 2005. 71 (7-8): p. 461-70.
Kudo, I. and M. Murakami, Prostaglandin e synthase, a terminal enzyme for prostaglandin E2 biosynthesis. J Biochem Mol Biol, 2005. 38(6): p. 633-8.
Samuelsson, B., R. Morgenstern, and P.J. Jakobsson, Membrane prostaglandin E synthase-1: a novel therapeutic target. Pharmacol Rev, 2007. 59(3): p. 207-24.
Zalin, R.J., The role of hormones and prostanoids in the in vitro proliferation and differentiation of human myoblasts. Exp Cell Res, 1987. 172(2): p. 265-81.

* cited by examiner

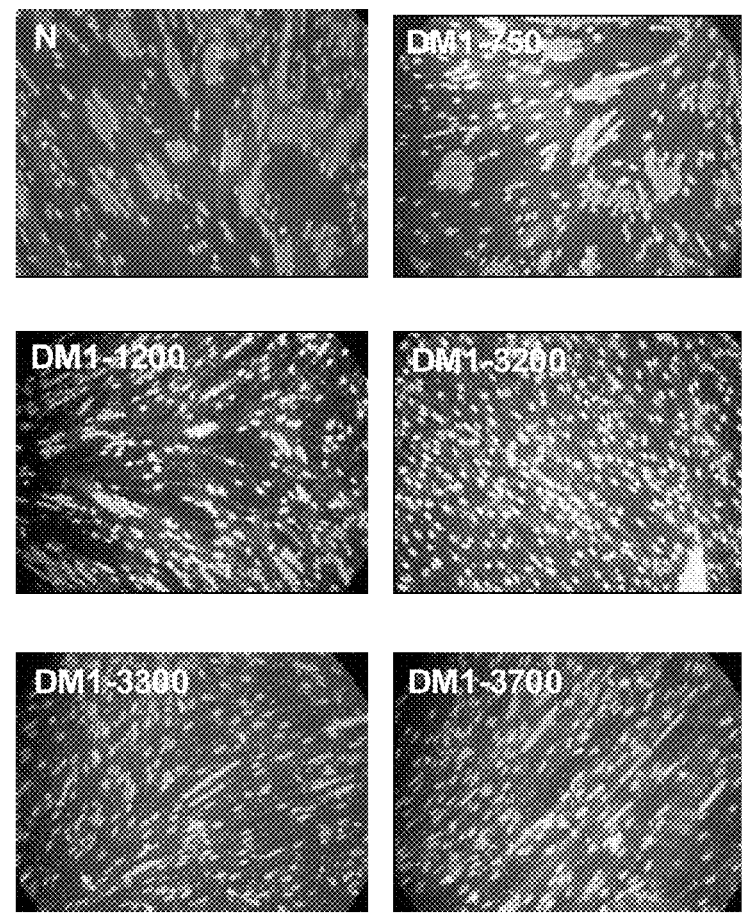
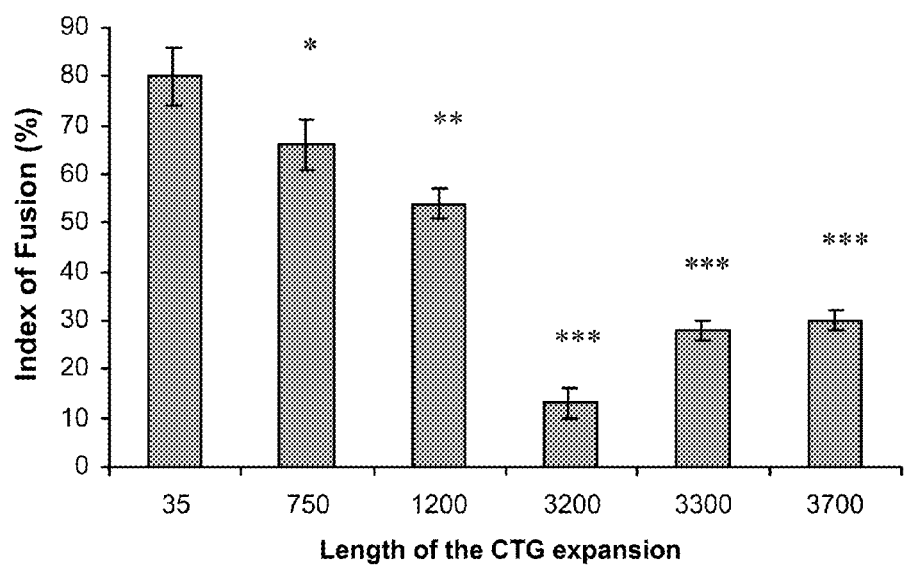
Fig. 1

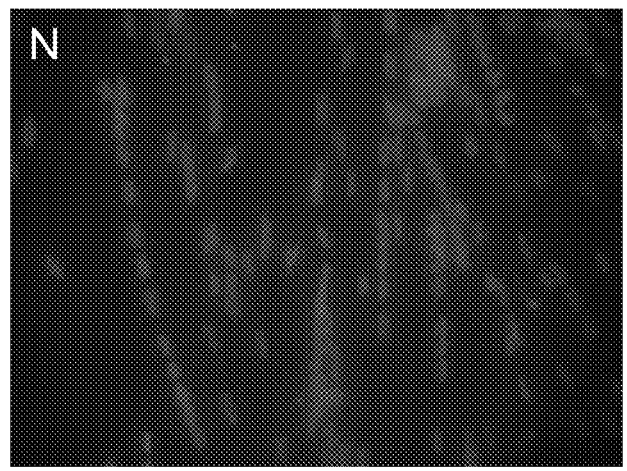
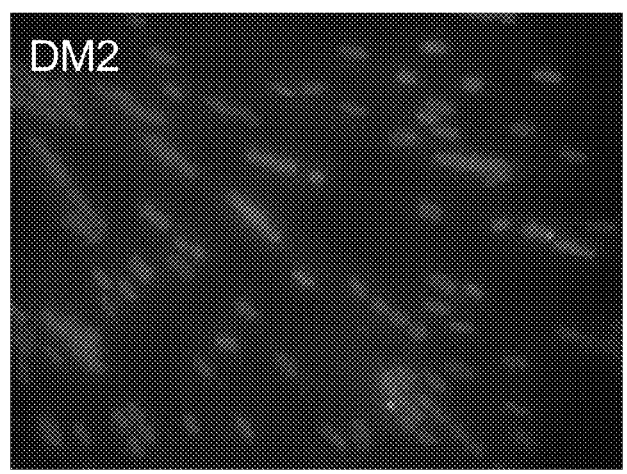
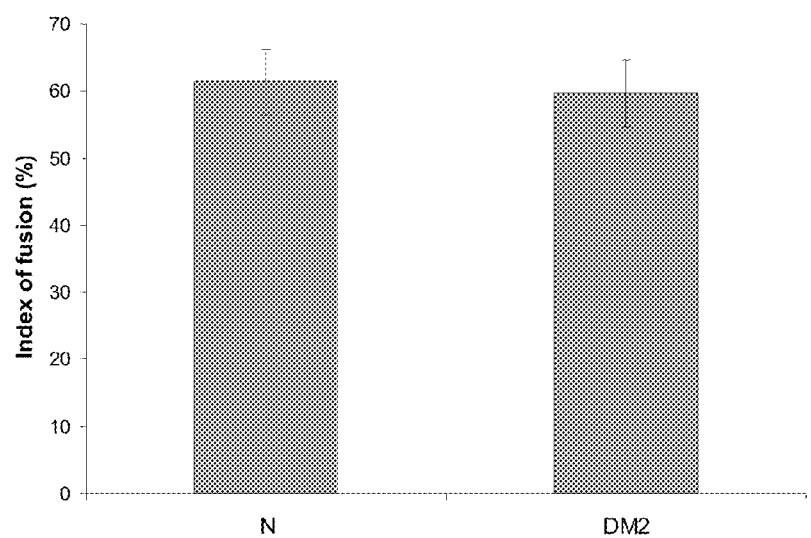
Fig. 4

A
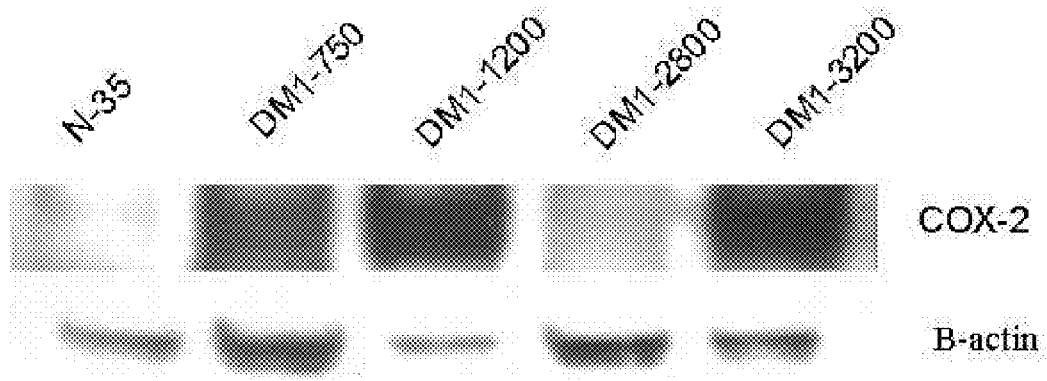
B
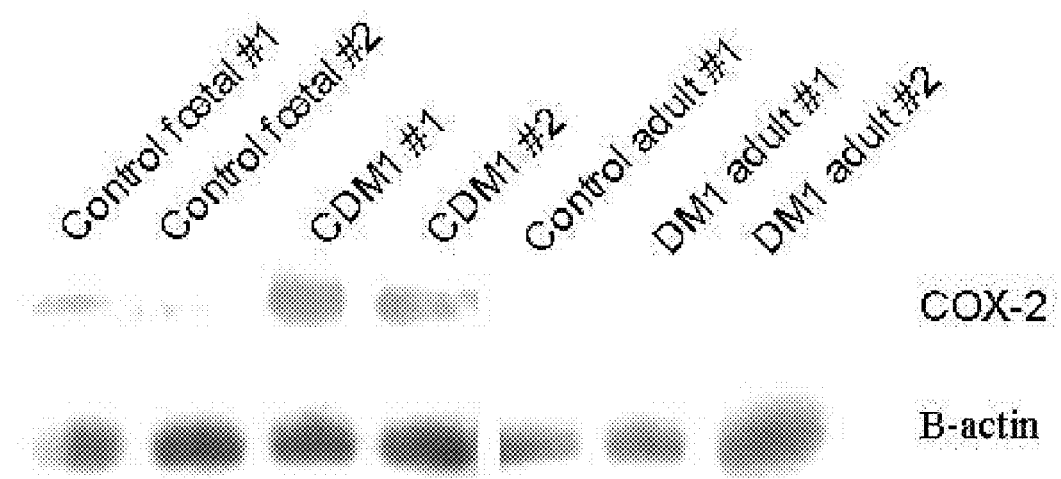
Fig. 8

A
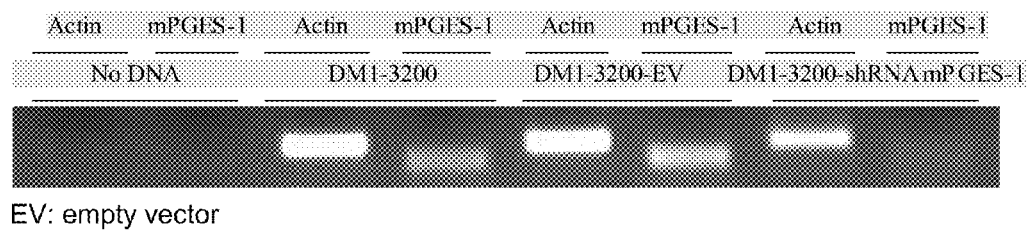
EV: empty vector
B
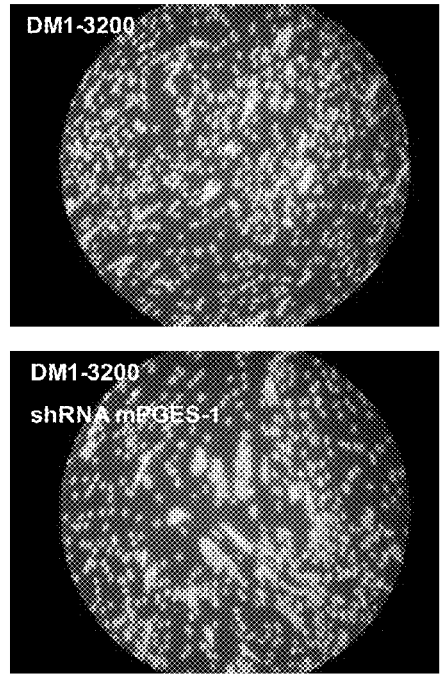
C
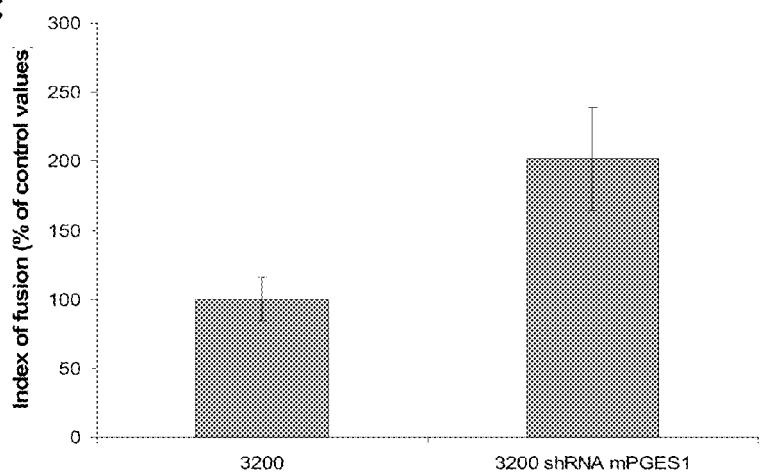
Fig. 9

A.

mPGES-1 nucleotide sequence (SEQ ID NO: 5), GenBank Accession No. NM_004878

```
   1 gctgctcctc tgtcgagctg atcacaccca cagttgagct gcgctggcca gagatgcctg
  61 cccacagcct ggtgatgagc agcccggccc tcccggcctt cctgctctgc agcacgctgc
 121 tggtcatcaa gatgtacgtg gtggccatca tcacgggcca agtgaggctg cggaagaagg
 181 cctttgccaa ccccgaggat gccctgagac acggaggccc ccagtattgc aggagcgacc
 241 ccgacgtgga acgctgcctc agggcccacc ggaacgacat ggagaccatc taccccttcc
 301 tttcctggg cttcgtctac tcctttctgg gtcctaaccc ttttgtcgcc tggatgcact
 361 tcctggtctt cctcgtgggc cgtgtggcac acaccgtggc ctacctgggg aagctgcggg
 421 cacccatccg ctccgtgacc tacaccctgg cccagctccc ctgcgcctcc atggctctgc
 481 agatcctctg ggaagcggcc cgccacctgt gaccagcagc tgatgcctcc ttggccacca
 541 gaccatgggc caagagccgc cgtggctata cctggggact tgatgttcct tccagattgt
 601 ggtgggccct gagtcctggt ttcctggcag cctgctgcgc gtgtgggtct ctggcacag
 661 tgggcctgtg tgtgtgccg tgtgtgtgta tgtttctt agcccccttgg
 721 attcctgcac gaagtggctg atgggaacca tttcaagaca gattgtgaag attgatagaa
 781 aatccttcag ctaaagtaac agagcatcaa aaacatcact ccctctccct ccctaacagt
 841 gaaaagagag aagggagact ctatttaaga ttcccaaacc taatgatcat ctgaatcccg
 901 ggctaagaat gcagactttt cagactgacc cagaaattc tggcccagcc aatctagagg
 961 caagcctggc catctgtatt ttttttttc caagacagag tcttgctctg ttgcccaagc
1021 tggagtgaag tggtacaatc tggctcactg cagcctccgc ctcccgggtt caagcgattc
1081 tcccgcctca gcctcctgag tagctgggat tacaggcgcg tatcaccata cccagctaat
1141 ttttgtattt ttagtagaga cgggttcacc atgttgccca ggagggtctc gaactcctgg
1201 cctcaagtga tccaccggcc tcggcctccc aaagtgctgg gatgacaggc atgaatcact
1261 gtgctcagcc accatctgga gttttaaaag gctcccatgt gagtccctgt gatggccagg
1321 ccaggggacc cctgccagtt ctctgtggaa gcaaggctgg ggtcttgggt tcctgtatgg
1381 tggaagctgg gtgagccaag gacagggctg gctcctctgc ccccgctgac gcttcccttg
1441 ccgttggctt tggatgtctt tgctgcagtc ttctctctgg ctcaggtgtg ggtgggaggg
1501 gcccacagga agctcagcct tctcctccca aggtttgagt ccctccaaag ggcagtgggt
1561 ggaggaccgg gagctttggg tgaccagcca ctcaaaggaa ctttctggtc ccttcagtat
1621 cttcaaggtt tggaaactgc aaatgtcccc ttgatgggga atccgtgtgt gtgtgtgtgt
1681 gtgtgtgtgt gtgtgtgtgt gtgtgtgttt tctcctagac ccgtgacctg agatgtgtga
1741 tttttagtca ttaaatggaa gtgtctgcca gctgggccca gcacctaaaa aaaaaaaaa
1801 aaaaa
```

B.

mPGES-1 amino acid sequence (SEQ ID NO: 6), GenBank Accession No. NP_004869

```
   1 mpahslvmss palpaflllcs tllvikmyvv aiitgqvrlr kkafanpeda lrhggpqycr
  61 sdpdverclr ahrndmetiy pflflgfvys flgpnpfvaw mhflvflvgr vahtvaylgk
 121 lrapirsvty tlaqlpcasm alqilweaar hl
```

Fig. 12

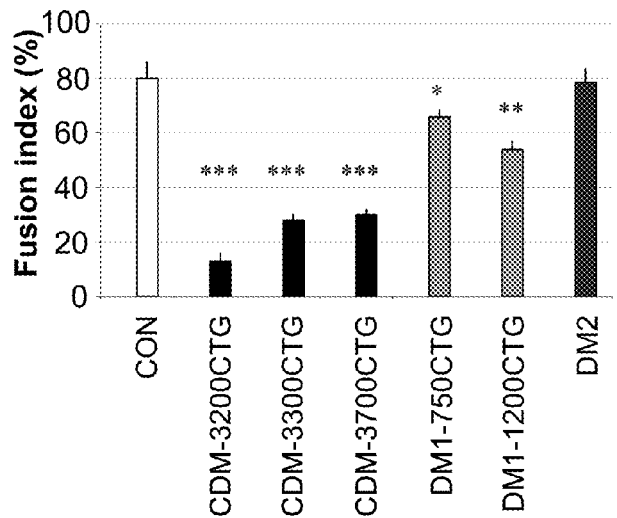
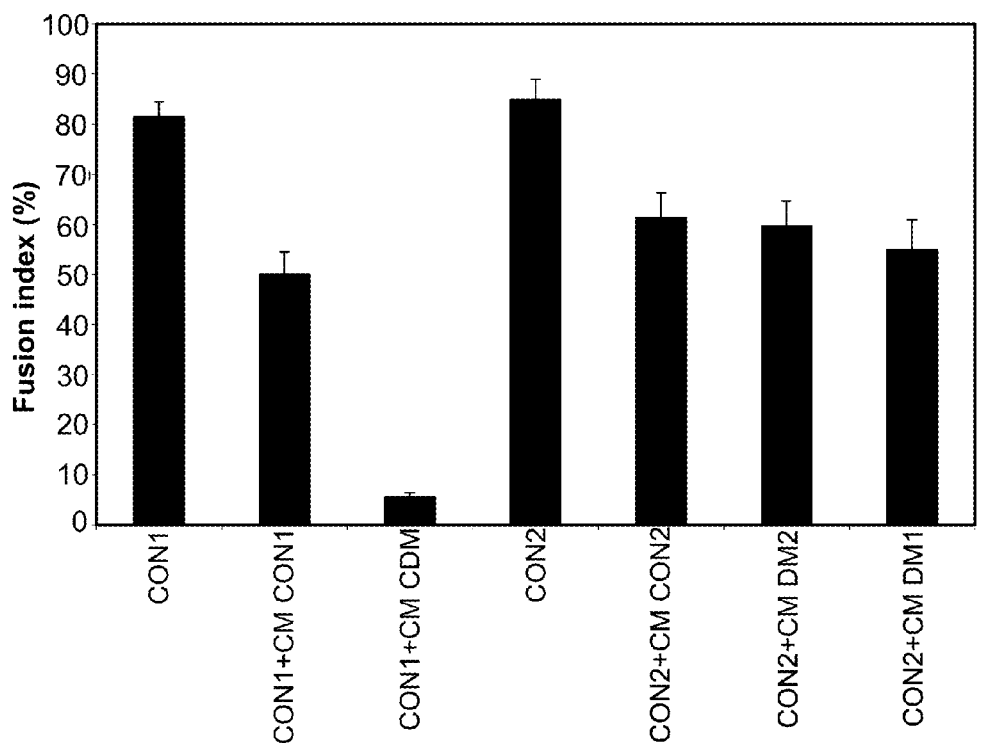
Fig. 13

C
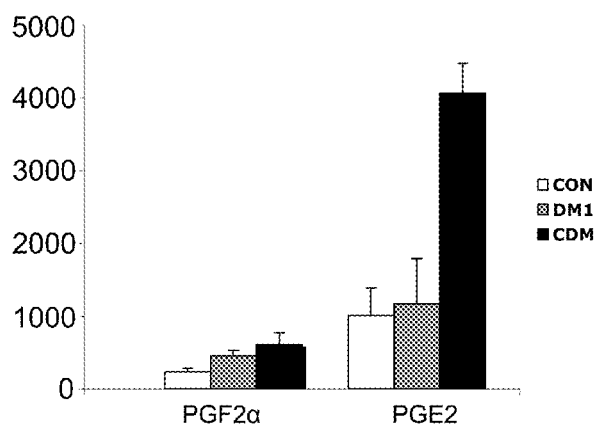
D.
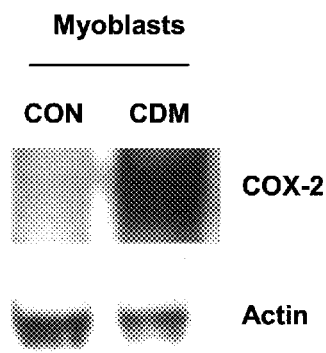
E.
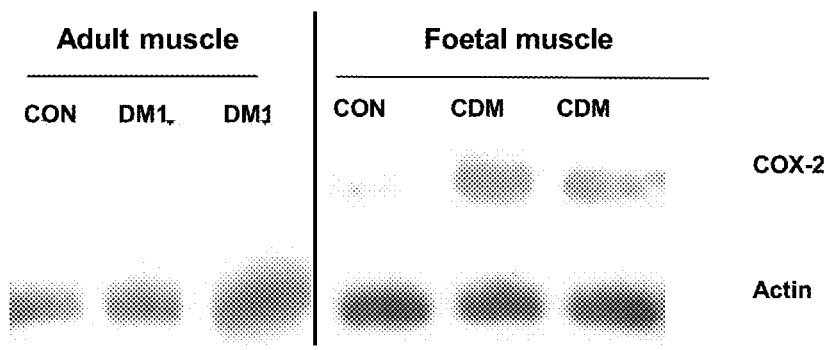
Fig. 13 (continued)

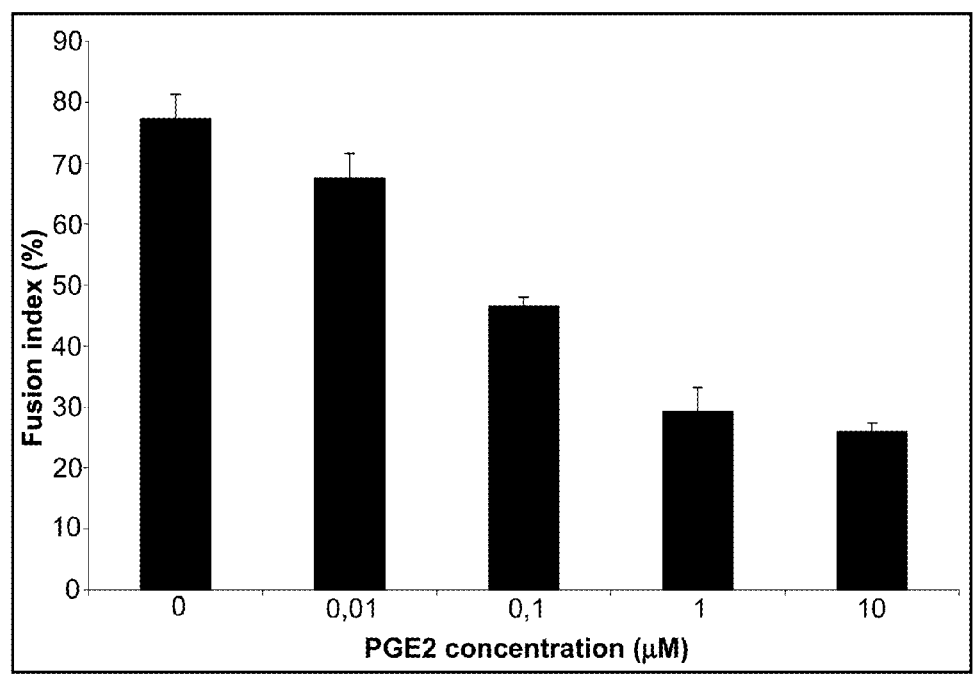
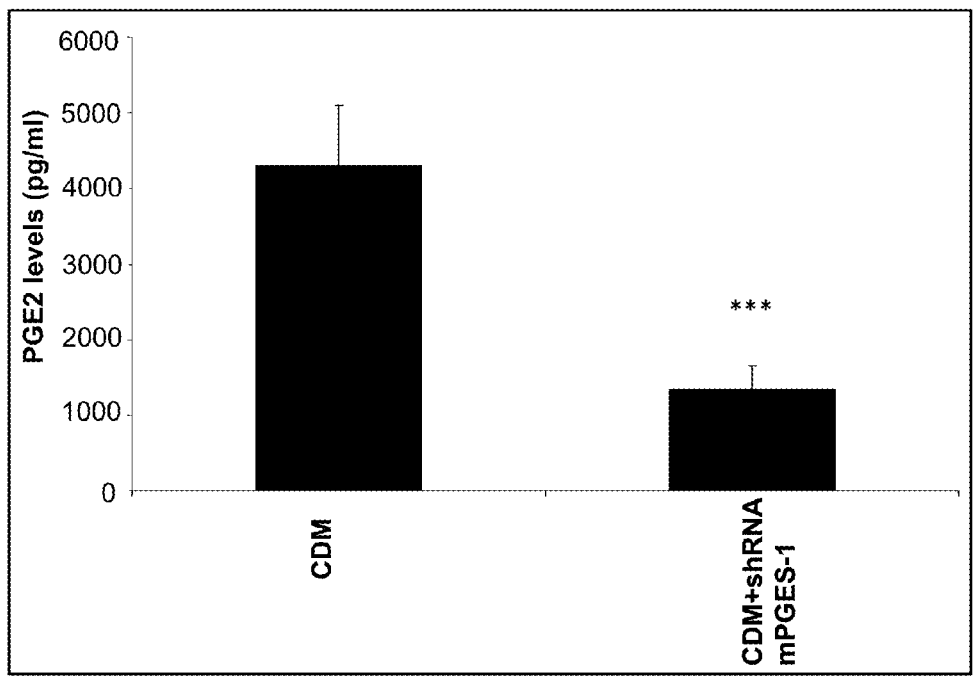
Fig. 14

C.
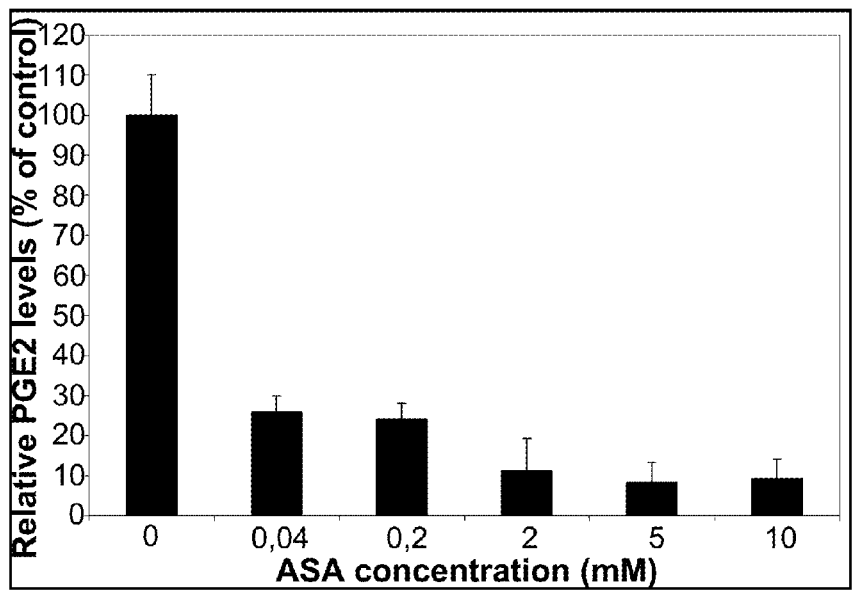
D.
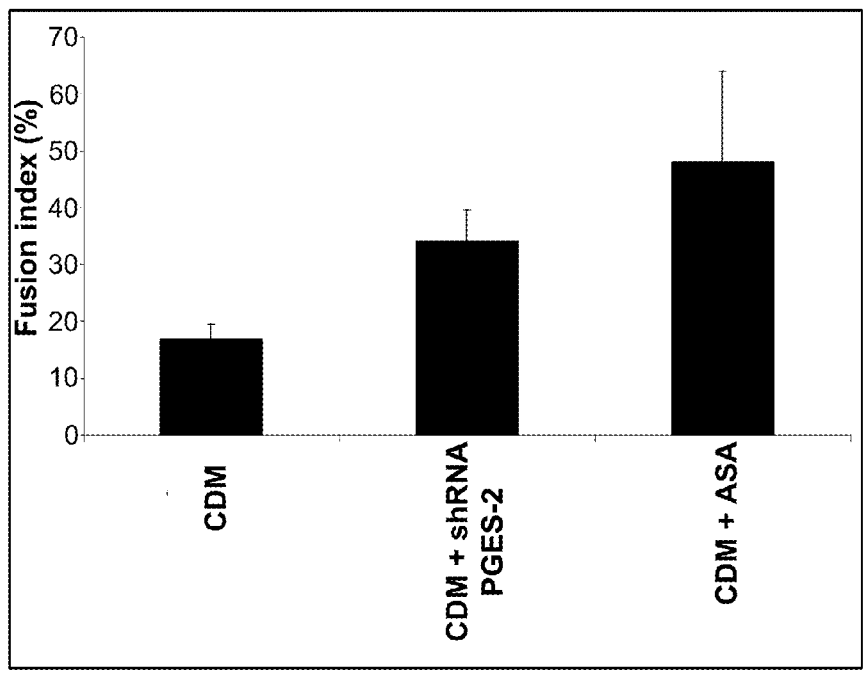
Fig. 14 (continued)

A.

COX-2/PTGS2 nucleotide sequence (SEQ ID NO: 11), GenBank Accession No. NM_000963

```
   1 caattgtcat acgacttgca gtgagcgtca ggagcacgtc caggaactcc tcagcagcgc
  61 ctccttcagc tccacagcca gacgccctca gacagcaaag cctacccccg cgccgcgccc
 121 tgcccgccgc tcggatgctc gcccgcgccc tgctgctgtg cgcggtcctg cgctcagcc
 181 atacagcaaa tccttgctgt tccacccat gtcaaaaccg aggtgtatgt atgagtgtgg
 241 gatttgacca gtataagtgc gattgtaccc ggacaggatt ctatgagaa aactgctcaa
 301 caccggaatt tttgacaaga ataaaattat ttctgaaacc cactccaaac acagtgcact
 361 acatacttac ccacttcaag ggattttgga acgttgtgaa taacattccc ttccttcgaa
 421 atgcaattat gagttatgtc ttgacatcca gatcacattt gattgacagt ccaccaactt
 481 acaatgctga ctatggctac aaaagctggg aagccttctc taacctctcc tattatacta
 541 gagcccttcc tcctgtgcct gatgattgcc cgactccctt gggtgtcaaa ggtaaaaagc
 601 agcttcctga ttcaaatgag attgtggaaa aattgcttct aagaagaaag ttcatccctg
 661 atccccaggg ctcaaacatg atgtttgcat ctttgccca gcacttcacg catcagtttt
 721 tcaagacaga tcataagcga gggccagctt tcaccaacgg ctgggccat ggggtggact
 781 taaatcatat ttacggtgaa actctggcta gacagcgtaa actgcgcctt ttcaaggatg
 841 gaaaaatgaa atatcagata attgatgtca agatgtatcc tcccacagtc aaagatactc
 901 aggcagagat gatctaccct cctcaagtcc ctgagcatct acggtttgct gtggggcagg
 961 aggtctttgg tctggtgcct ggtctgatga tgtatgccac aatctggctg cgggaacaca
1021 acagagtatg cgatgtgctt aaacaggagc atcctgaatg gggtgatgag cagttgttcc
1081 agacaagcag gctaatactg ataggagaga ctattaagat tgtgattgaa gattatgtgc
1141 aacacttgag tggctatcac ttcaaactga aatttgaccc agaactactt ttcaacaaac
1201 aattccagta ccaaaatcgt attgctgctg aatttaacac cctctatcac tggcatcccc
1261 ttctgcctga cacctttcaa attcatgacc agaaatacaa ctatcaacag tttatctaca
1321 acaactctat attgctggaa catggaatta cccagtttgt tgaatcatc accaggcaaa
1381 ttgctggcag ggttgctggt ggtaggaatg ttccaccgc agtacagaaa gtatcacagg
1441 cttccattga ccagagcagg cagatgaaat accagtcttt taatgagtac cgcaaacgct
1501 ttatgctgaa gccctatgaa tcatttgaag aacttacagg agaaaaggaa atgtctgcag
1561 agttggaagc actctatggt gacatcgatg ctgtggagct gtatcctgcc cttctggtag
1621 aaaagcctcg gccagatgcc atctttggtg aaaccatggt agaagttgga gcaccattct
1681 ccttgaaagg acttatgggt aatgttatat gttctcctgc ctactggaag ccaagcactt
1741 ttggtggaga gtgggttttt caaatcatca acactgcctc aattcagtct ctcatctgca
1801 ataacgtgaa gggctgtccc tttacttcat tcagtgttcc agatccagag ctcattaaaa
1861 cagtcaccat caatgcaagt tcttcccgct ccggactaga tgatatcaat cccacagtac
1921 tactaaaaga acgttcgact gaactgtaga agtctaatga tcatatttat ttatttatat
1981 gaaccatgtc tattaattta attatttaat aatatttata ttaaactcct tatgttactt
2041 aacatcttct gtaacagaag tcagtactcc tgttgcggag aaaggagtca tacttgtgaa
2101 gacttttatg tcactactct aaagattttg ctgttgctgt taagtttgga aaacagtttt
2161 tattctgttt tataaaccag agagaaatga gttttgacgt cttttactt gaatttcaac
2221 ttatattata agaacgaaag taaagatgtt tgaatactta aacactatca caagatggca
2281 aaatgctgaa agttttaca ctgtcgatgt ttccaatgca tcttccatga tgcattagaa
2341 gtaactgata tttgaaattt taaagtactt ttggttattt ttctgtcatc aaacaaaaac
2401 aggtatcagt gcattattaa atgaatattt aaattagaca ttaccagtaa tttcatgtct
2461 acttttaaa atcagcaatg aaacaataat ttgaaattc taaattcata gggtagaatc
2521 acctgtaaaa gcttgtttga tttcttaaag ttattaaact tgtacatata ccaaaaagaa
2581 gctgtcttgg atttaaatct gtaaatcag atgaaatttt actacaattg cttgttaaaa
2641 tattttataa gtgatgttcc ttttcacca agagtataaa cctttttagt gtgactgtta
2701 aaacttcctt ttaaatcaaa atgccaaatt tattaaggtg gtggagccac tgcagtgtta
2761 tctcaaaata agaatatttt gttgagatat tccagaattt gtttatatgg ctggtaacat
2821 gtaaatccta tatcagcaaa agggtctacc tttaaaataa gcaataacaa agaagaaaac
2881 caaattattg ttcaaattta ggtttaaact tttgaagcaa acttttttt atccttgtgc
2941 actgcaggcc tggtactcag attttgctat gaggttaatg aagtaccaag ctgtgcttga
```

Fig. 16

```
3001 ataacgatat gttttctcag attttctgtt gtacagttta atttagcagt ccatatcaca
3061 ttgcaaaagt agcaatgacc tcataaaata cctcttcaaa atgcttaaat tcatttcaca
3121 cattaatttt atctcagtct tgaagccaat tcagtaggtg cattggaatc aagcctggct
3181 acctgcatgc tgttcctttt cttttcttct tttagccatt ttgctaagag acacagtctt
3241 ctcatcactt cgtttctcct attttgtttt actagtttta agatcagagt tcactttctt
3301 tggactctgc ctatattttc ttacctgaac ttttgcaagt tttcaggtaa acctcagctc
3361 aggactgcta tttagctcct cttaagaaga ttaaaagaga aaaaaaaagg cccttttaaa
3421 aatagtatac acttatttta agtgaaaagc agagaatttt atttatagct aattttagct
3481 atctgtaacc aagatggatg caagaggct agtgcctcag agagaactgt acggggtttg
3541 tgactggaaa aagttacgtt cccattctaa ttaatgccct ttcttattta aaaacaaaac
3601 caaatgatat ctaagtagtt ctcagcaata ataataatga cgataatact tcttttccac
3661 atctcattgt cactgacatt taatggtact gtatattact taatttattg aagattatta
3721 tttatgtctt attaggacac tatggttata aactgtgttt aagcctacaa tcattgattt
3781 ttttttgtta tgtcacaatc agtatatttt ctttggggtt acctctctga atattatgta
3841 aacaatccaa agaaatgatt gtattaagat ttgtgaataa atttttagaa atctgattgg
3901 catattgaga tatttaaggt tgaatgtttg tccttaggat aggcctatgt gctagcccac
3961 aaagaatatt gtctcattag cctgaatgtg ccataagact gaccttttaa aatgttttga
4021 gggatctgtg gatgcttcgt taatttgttc agccacaatt tattgagaaa atattctgtg
4081 tcaagcactg tgggttttaa tattttttaaa tcaaacgctg attacagata atagtattta
4141 tataaataat tgaaaaaaat tttctttttgg gaagagggag aaaatgaaat aaatatcatt
4201 aaagataact caggagaatc ttctttacaa ttttacgttt agaatgttta aggttaagaa
4261 agaaatagtc aaatatgcttg tataaaacac tgttcactgt tttttttaaa aaaaaaactt
4321 gatttgttat taacattgat ctgctgacaa aacctgggaa tttgggttgt gtatgcgaat
4381 gtttcagtgc ctcagacaaa tgtgtattta acttatgtaa aagataagtc tggaaataaa
4441 tgtctgttta ttttttgtact attta
```

B.

COX-2/PTGS2 amino acid sequence (SEQ ID NO: 12), GenBank Accession No.
NP_000954

```
  1 mlarallica vlalshtanp ccshpcqnrg vcmsvgfdqy kcdctrtgfy gencstpefl
 61 triklflkpt pntvhyilth fkgfwnvvnn ipflrnaims yvltsrshli dspptynady
121 gyksweafsn lsyytralpp vpddcptplg vkgkkqlpds neiveklllr rkfipdpqgs
181 nmmfaffaqh fthqffktdh krgpaftngl ghgvdlnhiy getlarqrkl rlfkdgkmky
241 qiidgemypp tvkdtqaemi yppqvpehlr favgqevfgl vpglmmyati wlrehnrvcd
301 vlkqehpewg deqlfqtsrl iligetikiv iedyvqhlsg yhfklkfdpe llfnkqfqyq
361 nriaaefntl yhwhpllpdt fqihdqkyny qqfiynnsil lehgitqfve sftrqiagrv
421 aggrnvppav qkvsqasidq srqmkyqsfn eyrkrfmlkp yesfeeltge kemsaeleal
481 ygdidavely pallvekprp daifgetmve vgapfslkgl mgnvicspay wkpstfggev
541 gfqiintasi qslicnnvkg cpftsfsvpd peliktvtin asssrsgldd inptvllker
601 stel
```

PROSTAGLANDIN E2 MODULATION AND USES THEREOF

CROSS REFERENCE TO RELATED APPLICATIONS

This application is a Divisional Application of U.S. application Ser. No. 12/205,194, filed Sep. 5, 2008, which claims the benefit, under 35 U.S.C. §119(e), of U.S. Provisional Application Ser. No. 60/971,392, filed Sep. 11, 2007, and which applications are incorporated herein by reference.

SEQUENCE LISTING

Pursuant to 37 C.F.R. 1.821(c), a sequence listing is submitted herewith as an ASCII compliant text file named "11229_301-seq_listing_ST25", which was created on Jun. 15, 2010 and has a size of 24,700 bytes. The content of the aforementioned file named "11229_301-seq_listing_ST25" is hereby incorporated by reference in its entirety.

FIELD OF THE INVENTION

The present invention relates to changes in/modulation of prostaglandin $E_2$ ($PGE_2$) levels, and uses thereof for prognosis, diagnosis, prevention and treatment of myotonic dystrophy type 1 (DM1), and more particularly for the prognosis, diagnosis, prevention and treatment of the congenital form of myotonic dystrophy type 1 (cDM1).

BACKGROUND OF THE INVENTION

Myotonic dystrophy type 1 (DM1), also known as Steinert's disease, is an autosomal, dominantly inherited neuromuscular disorder with a global incidence of 1 per 8000 (Harper P S: Myotonic Dystrophy $2^{nd}$ ed., 1989, W.B. Saunders, London). The mutation responsible for the disease is a $(CUG)_n$ repeat expansion in the 3' untranslated region of the DM protein kinase (DMPK) gene (Mahadevan et al., 1992. *Science* 255:1253-1255; Fu et al., 1992. *Science* 255:1256-1258; Brook et al., 1992. *Cell* 68:799-808). This repeat ranges in size from 5-37 repeats in the normal population to between 50-1000 repeats in adult onset cases (Harper, supra).

Adult onset DM1 is primarily characterized by myotonia, muscle wasting, and weakness, but also affects a number of organs and results in cataracts, cardiac conduction abnormalities, testicular atrophy, male baldness, and insulin resistance (Harper, supra). The main clinical symptoms of congenital myotonic dystrophy (cDM1), the most severe form of DM1, are hypotonia and neonatal respiratory distress, the latter being the major cause of mortality in cDM1 infants. Furthermore, children affected by the disease frequently suffer from mental retardation and delayed motor milestones. It has been shown that cDM1 is usually associated with extremely large CTG expansions (>1500 CTG) and evidence of delayed or arrested muscle maturation (Furling et al., 2003. *Am J Pathol.* 162:1001-1009; Tsilfidis et al., 1992. *Nat Genet* 1:192-195; Hunter et al. 1992. *J Med Genet* 29:774-779). Currently there is no curative therapy for this disease, and symptomatic or rehabilitation treatments are only available for the adult form of DM1.

Thus, there is a need for novel methods and products for the prognosis, diagnosis and prevention/treatment of cDM1.

SUMMARY OF THE INVENTION

The present invention relates to changes in/modulation of prostaglandin $E_2$ ($PGE_2$) levels, and uses thereof for prognosis, diagnosis, prevention and treatment of myotronic dystrophy type 1 (DM1), and more particularly for the prognosis, diagnosis, prevention and treatment of the congenital form of myotronic dystrophy type 1 (cDM1).

In an aspect, the present invention provides a method for preventing and/or treating congenital myotonic dystrophy type 1 (cDM1) in a subject comprising inhibiting the biosynthesis or activity of prostaglandin $E_2$ ($PGE_2$) in the subject.

In another aspect, the present invention provides a use of an inhibitor of $PGE_2$ biosynthesis or activity for the prevention and/or treatment of cDM1 in a subject.

In another aspect, the present invention provides a use of an inhibitor of $PGE_2$ biosynthesis or activity for the preparation of a medicament for the prevention and/or treatment of cDM1 in a subject.

In an embodiment, the above-mentioned inhibition is through the inhibition of the expression and/or activity of a mediator involved in $PGE_2$ biosynthesis.

In another embodiment, the above-mentioned method comprises the administration, to the subject, of a therapeutically-effective amount of an inhibitor of expression and/or activity of a mediator involved in $PGE_2$ biosynthesis.

In another aspect, the present invention provides a method for treating congenital myotonic dystrophy type 1 (cDM1) in a subject, said method comprising:
(a) assessing the level or activity of (i) $PGE_2$, (ii) a mediator involved in $PGE_2$ biosynthesis, or (iii) both (i) and (ii) in a biological sample obtained from said subject; and
(b) administering an inhibitor of expression and/or activity of a mediator involved in $PGE_2$ biosynthesis to said subject if said level or activity is increased relative to a corresponding reference level or activity.

In an other aspect, the present invention provides a method for treating congenital myotonic dystrophy type 1 (cDM1) in a subject, said method comprising: selecting or identifying a subject suffering from cDM1; and administering an inhibitor of expression and/or activity of a mediator involved in $PGE_2$ biosynthesis to said subject suffering from cDM1.

In another aspect, the present invention provides a method (in vitro or in vivo) for increasing the fusion and/or differentiation of cDM1 muscle cells (e.g., myoblasts) comprising contacting said cells with an inhibitor of the biosynthesis or activity of prostaglandin $E_2$ ($PGE_2$).

In another aspect, the present invention provides a use of an inhibitor of the biosynthesis or activity of prostaglandin $E_2$ ($PGE_2$) for increasing the fusion and/or differentiation of cDM1 muscle cells (e.g., myoblasts).

In another aspect, the present invention provides a use of an inhibitor of the biosynthesis or activity of prostaglandin $E_2$ ($PGE_2$) for the preparation of a medicament for increasing the fusion and/or differentiation of cDM1 muscle cells (e.g., myoblasts).

In an embodiment, the above-mentioned inhibitor is selected from a nonsteroidal anti-inflammatory drug (NSAID) and a cyclooxygenase (COX) inhibitor. In a further embodiment, the above-mentioned inhibitor is acetylsalicylic acid.

In another embodiment, the above-mentioned NSAID is a COX-2 inhibitor.

In yet another embodiment, the above-mentioned mediator involved in $PGE_2$ biosynthesis is an inducible enzyme involved in $PGE_2$ biosynthesis. In a further embodiment, the above-mentioned mediator is microsomal PGE synthase-1 (mPGES-1).

In an embodiment, the above-mentioned inhibition is with a short hairpin RNA (shRNA) or a small interfering RNA (siRNA). In a further embodiment, the above-mentioned shRNA is encoded by a nucleic acid comprising the nucleotide sequence of SEQ ID NO:3 or SEQ ID NO:4.

In another embodiment, the above-mentioned inhibitor blocks the expression and/or activity of a mediator involved in $PGE_2$ biosynthesis.

In another aspect, the present invention provides a method of prognosticating or diagnosing cDM1 in a first subject, the method comprising comparing the level or activity of (i) $PGE_2$, (ii) a mediator involved in $PGE_2$ biosynthesis, or (iii) both (i) and (ii) in a biological sample from the first subject with a corresponding reference level or activity; and prognosticating or diagnosing cDM1 in accordance with the comparison.

In an embodiment, the above-mentioned reference level or activity is the level or activity of (i) $PGE_2$, (ii) a mediator involved in $PGE_2$ biosynthesis, or (iii) both (i) and (ii) in a corresponding biological sample from a second subject not suffering from cDM1, and wherein a higher level or activity in the sample from the first subject relative to the level in the sample from the second subject is indicative that the first subject has or is at risk of developing cDM1.

In another embodiment, the above-mentioned reference level or activity is the level or activity of (i) $PGE_2$, (ii) a mediator involved in $PGE_2$ biosynthesis, or (iii) both (i) and (ii) in a corresponding biological sample from a second subject suffering from cDM1, and wherein a substantially similar level or activity in the sample from the first subject relative to the level or activity in the sample from the second subject is indicative that the first subject has or is at risk of developing cDM1.

In another aspect, the present invention provides a method for determining whether a test compound is useful for preventing and/or treating cDM1, the method comprising: (a) contacting a biological sample from a subject at risk of or suffering from cDM1 with the test compound; and (b) determining the level and/or activity of (i) $PGE_2$, (ii) a mediator involved in $PGE_2$ biosynthesis, or (iii) both (i) and (ii); wherein a decrease in the level and/or activity in the presence relative to the absence of the test compound is indicative that the test compound is useful for preventing and/or treating cDM1.

In another aspect, the present invention provides a method for determining whether a test compound is useful for preventing and/or treating cDM1, the method comprising assaying the level and/or activity of (i) $PGE_2$, (ii) a mediator involved in $PGE_2$ biosynthesis, or (iii) both (i) and (ii), in the presence versus in the absence of the test compound, wherein a decrease in the level and/or activity in the presence relative to the absence of the test compound is indicative that the test compound is useful for preventing and/or treating cDM1.

In an embodiment, the above-mentioned mediator is COX-2. In another embodiment, the above-mentioned COX-2 comprises the amino acid sequence of residues 18-604 of the amino acid sequence of SEQ ID NO: 12 and the method comprises determining the level or activity of a polypeptide comprising residues 18-604, or a fragment thereof, of the amino acid sequence of SEQ ID NO: 12. In another embodiment, the above-mentioned method comprises determining the level of a nucleic acid encoding the above-mentioned polypeptide, or a fragment thereof. In a further embodiment, the above-mentioned nucleic acid comprises the nucleotide sequence of SEQ ID NO:11.

In another embodiment, the above-mentioned assaying comprises contacting the test compound with a cell comprising (i) $PGE_2$, (ii) a mediator involved in $PGE_2$ biosynthesis, or (iii) both (i) and (ii).

In another embodiment, the above-mentioned assaying comprises contacting the test compound with a mediator involved in $PGE_2$ biosynthesis.

In an embodiment, the above-mentioned mediator is COX-2 or mPGES-1.

In an embodiment, the above-mentioned biological sample is a muscle cell sample or a muscle cell precursor sample. In a further embodiment, the above-mentioned muscle cell precursor sample is a myoblast sample.

In an embodiment, the above-mentioned method further comprises: (d) contacting a myoblast sample from a subject at risk of or suffering from cDM1 with the test compound; (e) culturing the myoblasts under conditions suitable for myoblast differentiation; and (f) determining the level of differentiation of the myoblast; wherein an increase in the level of differentiation of the myoblasts in the presence relative to the absence of the test compound is indicative that the test compound is useful for preventing and/or treating cDM1.

In an embodiment, the above-mentioned level of differentiation is determined by measuring the index of fusion of the myoblasts after the culturing.

In another aspect, the present invention provides a composition for prevention and/or treatment of cDM1 in a subject, comprising an inhibitor of $PGE_2$ biosynthesis or activity and a pharmaceutically acceptable carrier. In an embodiment, the above-mentioned inhibitor is acetylsalicylic acid.

In another aspect, the present invention provides a method for prevention and/or treatment of cDM1 in a subject, comprising the administration of a therapeutically-effective amount of acetylsalicylic acid to the subject.

In another aspect, the present invention provides a use of acetylsalicylic acid for the prevention and/or treatment of cDM1.

In another aspect, the present invention provides a use of acetylsalicylic acid for the preparation of a medicament for prevention and/or treatment of cDM1.

In another aspect, the present invention provides acetylsalicylic acid for the prevention and/or treatment of cDM1.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1 shows the relationship between the length of CTG expansion and the fusion of myoblasts;

FIG. 4 shows that DM2-conditioned medium has no effect on the fusion or normal myoblasts;

FIG. 8 shows the expression of COX-2 in A) DM1 cells (in vitro) and B) cDM1 and adult DM1 muscle biopsies (in vivo). COX-2 expression was measured in DM1 cells (upper panel), in cDM1 and adult DM1 biopsies (lower panel). 20 µg of total protein from cells kept in proliferative state or in muscles biopsies were loaded on a 10% acrylamide SDS-PAGE gel. β-actin level was used as a control for loading;

FIG. 9 shows the restoration of DM1 myoblast differentiation in the presence of a shRNA directed against mPGES-1. (A) Specific inhibition of mPGES-1 expression in the presence of the shRNA. (B) and (C) Comparison of the index of fusion of DM1 myoblasts in presence (lower panel in (B), right bar on the graph in (C)) and absence (upper panel in (B), left bar on the graph in (C)) of the shRNA directed against mPGES-1. To measure the levels of mPGES-1 mRNA in untreated cells, in cells infected with lentivirus that contains no shRNAs and cells infected with lentivirus that allowed expression of shRNA against mPGES-1 in human myoblasts, mRNA encoding mPGES-1 was converted to complementary DNA using the Quantitech™ Reverse Transcription kit (Qiagen Cat. No. 205311) and then amplified by PCR using the following primers TGCATTCTTTGCCCAGCACT (SEQ ID NO: 1) and AAAGGCGCAGTTTACGCTGT (SEQ ID NO: 2). To study the effect of shRNA against mPGES-1 mRNA on cDM1 myoblast differentiation, CDM-1 cells were infected in the proliferative state and differentiated for 3 days. For the quantitation of the fusion index, the number of nuclei in multinucleated myotubes is expressed as a percentage of the total number of nuclei. About 1000 nuclei from three independent experiments were counted;

FIG. 12 shows the nucleotide ((A); SEQ ID NO: 5) and amino acid ((B); SEQ ID NO: 6) sequences of human mPGES-1. The coding sequence is in bold in the nucleotide sequence depicted in (A);

FIG. 13 shows in vitro and in vivo studies showing increased levels in prostaglandin-$E_2$ ($PGE_2$) in muscle cells derived from congenital myotonic dystrophy type 1. (A) Inhibition of the fusion of 3 different cDM1 myoblast cell lines compared to controls, DM1 and DM2 myoblasts. Statistical analysis were performed by Student t test. * p=0.003,  p=0.002, * p=0.0001. (B) Inhibition of the fusion of normal fetal myoblasts (CON1) by conditioned medium collected from fetal cDM1 myoblasts but not from normal myoblasts. No effect of conditioned medium collected from adult normal, DM1 or DM2 myoblast cultures on the fusion of adult normal myoblasts (CON2), *** p=0.0001. (C) Specific increased levels in $PGE_2$ in the medium derived from cDM1 cell cultures whereas no effect was observed with conditioned medium by adult DM1 myoblast cultures. P<0.0001. (D, E) The increased levels in $PGE_2$ is associated with increased levels in Cox-2 enzyme protein in cDM1 myoblasts and in vivo in the skeletal muscle of patients with cDM1;

FIG. 14 shows that inhibition of $PGE_2$ synthesis restores myogenic differentiation of cDM1 myoblasts. (A) Treatment of cDM1 myoblasts with increasing doses of $PGE_2$ inhibit myogenic fusion with maximal effect occurring at 1 µM. (B) Inhibition of mPGES-1 mRNAs by shRNA (insert) is associated with a 4-fold decrease in the levels of $PGE_2$ (lower panel, * p=0.0002) and with a 2-fold increase of the index of fusion of cDM1 myoblasts (, p<0.005) (D). (C) Treatment of cDM1 myoblasts with increasing doses of acetylsalicylic acid (ASA) decreased the levels of $PGE_2$ in the cultures medium of cDM1 myoblasts and led to a 4-fold increase of the index of fusion of these cells (***, p<0.001) (D);

FIG. 16 shows the nucleotide ((A); SEQ ID NO: 11) and amino acid ((B); SEQ ID NO: 12) sequences of human cyclooxygenase-2 (also known as prostaglandin-endoperoxide synthase 2). The coding sequence is in bold in the nucleotide sequence depicted in (A), and the sequence corresponding to the mature polypeptide is in bold in the amino acid sequence depicted in (B);

DESCRIPTION OF ILLUSTRATIVE EMBODIMENTS

Figure 2:
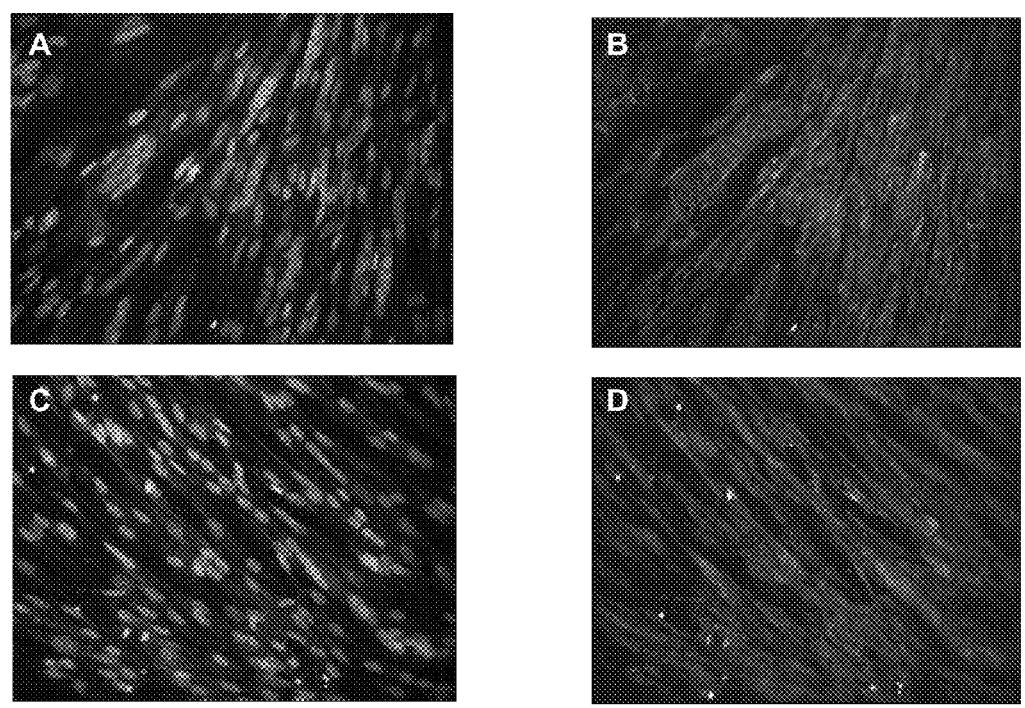
FIG. 2 shows the alteration of the fusion of normal myoblasts co-cultured with cDM1 myoblasts (DM1-3200 myoblasts). (A) and (B) GFP-positive normal myoblasts co-cultured with normal myoblasts. (A) DAPI staining and (B) GFP-positive cells. (C) and (D) GFP-positive cells co-cultured with cDM1 myoblasts. (C) DAPI staining and (D) GFP-positive cells.

Described herein are methods, uses, kits and products for the prognosis, diagnosis, prevention and treatment of myotronic dystrophy type 1 (DM1), and more particularly for the prognosis, diagnosis, prevention and treatment of the congenital form of myotronic dystrophy type 1 (cDM1), based on changes in/modulation of prostaglandin $E_2$ ($PGE_2$).

Prostaglandins are a class of eiconisoids that play an important role in several biological/physiological processes including pain, fever and inflammation. They are synthesized from arachidonic acid, and possess a five-membered ring of carbon atoms that had formed part of the chain of arachidonic acid. Prostaglandins typically act locally, near the site of their synthesis. $PGE_2$ has been demonstrated to be an important pro-inflammatory and hyperalgesia-inducing lipid mediator. The synthesis of $PGE_2$ is catalyzed by two classes of enzymes. The first class of enzymes, cyclooxygenases (COX) (also known as prostaglandin-endoperoxide synthase, PTGS), generates prostaglandin $H_2$ ($PGH_2$) using an arachidonic acid precursor released from membrane phospholipids. Examples of cyclooxygenases include COX-1 (PTGS1) and COX-2 (PTGS2). The second class of enzymes, $PGE_2$ synthases, produces $PGE_2$ using a $PGH_2$ precursor. Examples of $PGE_2$ synthases include cytosolic $PGE_2$ synthase (cPGES) and microsomal $PGE_2$ synthases (mPGES), such as mPGES-1 and mPGES-2 (Murakami et al., 2004. *Progress in Lipid Research* 43: 3-35). $PGE_2$ exerts its actions via four types of receptors: EP1, EP2, EP3, and EP4.

$PGE_2$ is produced by two separate pathways. The first pathway produces $PGE_2$ at a basal level. Constitutively-produced PGES is expressed in the cytosol (cPGES) under basal conditions in a wide variety of mammalian cells. Under basal conditions, COX-1 stimulates the production of $PGH_2$ from arachidonic acid, which in turn produces basal levels of $PGE_2$ upon activation with cPGES. The second pathway produces $PGE_2$ after induction by external stimulus such as cytokines and is localized to the microsomal compartment of the cell; hence is termed mPGES. Upon stimulation by a proinflammatory stimulus such as cytokines, COX-2 reacts with arachidonic acid to produce $PGH_2$, which in turn induces mPGES to produce $PGE_2$ from $PGH_2$ (Murakami et al., 2004. supra).

In the studies described herein, Applicant has shown that muscle cells/myoblasts from subjects affected by cDM1 express higher levels of prostaglandin $E_2$ ($PGE_2$) and cyclooxygenase-2 (COX-2; an enzyme involved in $PGE_2$ biosynthesis) as compared to myoblasts from DM1 or normal subjects. Applicant has further demonstrated that the fusion/differentiation of normal myoblasts is significantly altered in the presence of $PGE_2$, and that the inhibition of mediators involved in $PGE_2$ biosynthesis in cDM1 myoblasts restores their ability to fuse/differentiate.

Accordingly, in a first aspect, the present invention provides a method for preventing and/or treating the congenital form of myotonic dystrophy type 1 (cDM1) in a subject comprising inhibiting the biosynthesis or activity of prostaglandin $E_2$ ($PGE_2$) in said subject.

In another aspect, the present invention provides the use of an inhibitor of $PGE_2$ biosynthesis or activity for the prevention and/or treatment of cDM1 in a subject.

In another aspect, the present invention provides the use of an inhibitor of $PGE_2$ biosynthesis or activity for the preparation of a medicament for the prevention and/or treatment of cDM1 in a subject.

As used herein "inhibition of $PGE_2$ biosynthesis or activity" refers to any method which decreases the levels of $PGE_2$ or blocks its biological/physiological activity; and "inhibitor of $PGE_2$ biosynthesis or activity" refers to any agent, compound or composition of matter which decreases the levels of $PGE_2$ or blocks its biological/physiological activity. This includes, for example, any method or compound that: (1) inhibits the level or activity of a precursor of $PGE_2$ (e.g., arachidonic acid, $PGG_2$, $PGH_2$); (2) inhibits the level or activity of a mediator (e.g., an enzyme, a co-factor) involved in the biosynthesis of $PGE_2$ (e.g., cytosolic phospholipase $A_2$, COX-1, COX-2, Peroxidase, PGE Synthases (e.g., mPGES-1, mPGES-2)); (3) inhibits the activity of $PGE_2$, for example, by blocking the binding or activity of $PGE_2$ to one or more of its receptors (e.g., $PGE_2$-EP1, $PGE_2$-EP2, $PGE_2$-EP3 and/or $PGE_2$-EP4), by increasing/stimulating its degradation (e.g., decreasing its half-life) or by altering the normal localization (e.g., in a cell, tissue and/or organ) of PGE2 and/or of a mediator involved in the biosynthesis of $PGE_2$.

Several methods and compounds suitable for inhibiting $PGE_2$ biosynthesis or activity have been described. Antagonists of $PGE_2$ activity are described, for example, in WO 00/16760, WO 00/18744 and U.S. Patent publication No. 2007/0142638. Blocking antibodies directed against $PGE_2$ are described, for example in Portanova et al., 1996. *J. Exp. Med.* 184: 883-91. Inhibitors of PGE synthases (mPGES-1) are described in U.S. Patent publication No. 2007/0208017. Numerous inhibitors of the COX enzymes (nonselective COX inhibitors as well as COX-1 or COX-2 selective inhibitors) have been described (e.g., acetylsalicylic acid (Aspirin™), as well as derivatives and analogues thereof), several of which are commercially available.

The inhibition of the expression and/or activity of a polypeptide (e.g., an enzyme) involved in the biosynthesis of $PGE_2$ may be achieved either at the nucleic acid or polypeptide level using well-known techniques. For example, the inhibition of expression or activity of the polypeptide may be achieved, for example, (1) by inhibiting the transcription of the gene encoding the polypeptide; (2) by inhibiting, destabilizing or inducing the degradation of the mRNA encoding the polypeptide (e.g., using RNA interference; antisense oligonucleotides); (3) by introducing a mutation in a nucleic acid encoding the polypeptide (4) by blocking the translation of the mRNA into the polypeptide it encodes (e.g., using antisense oligonucleotides); (5) by inducing the degradation of the polypeptide; (6) by blocking a region of the polypeptide essential for its activity (e.g., the active site of an enzyme, a region involved in ligand or co-factor binding); and (7) by antagonizing the biological/physiological effect of the polypeptide.

In an embodiment, the above-mentioned inhibition is achieved through the inhibition of the expression and/or activity of a mediator involved in $PGE_2$ biosynthesis. In a further embodiment, the above-mentioned inhibition is with a nonsteroidal anti-inflammatory drug (NSAID; e.g., acetylsalicylic acid (Aspirin™)). In a further embodiment, the above-mentioned NSAID is a cyclooxygenase (COX) inhibitor (e.g., COX-1 and/or COX-2 inhibitor). In a further embodiment, the above-mentioned COX inhibitor is acetylsalicylic acid (Aspirin™).

In another embodiment, the above-mentioned mediator involved in PGE$_2$ biosynthesis is an inducible enzyme involved in PGE$_2$ biosynthesis. In a further embodiment, the above-mentioned mediator/enzyme is microsomal PGE synthase-1 (mPGES-1). In an embodiment, the above-mentioned inhibition is mediated by RNA interference (RNAi).

"RNA interference" or "RNAi" refers to a biological process of inhibiting or downregulating gene expression in a cell as is generally known in the art and which is mediated by short interfering nucleic acid molecules, see for example Zamore and Haley, *Science,* 309:1519; Vaughn and Martienssen, *Science,* 309:1525; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914). In addition, as used herein, the term RNAi is meant to be equivalent to other terms used to describe sequence-specific RNA interference, such as post-transcriptional gene silencing, translational inhibition, transcriptional inhibition, or epigenetics. For example, small interfering nucleic acid (siNA) molecules of the invention can be used to epigenetically silence genes at both the post-transcriptional level or the pre-transcriptional level. In a non-limiting example, epigenetic modulation of gene expression by siNA molecules of the invention can result from siNA mediated modification of chromatin structure or methylation patterns to alter gene expression. In another non-limiting example, modulation of gene expression by siNA molecules of the invention can result from siNA mediated cleavage of RNA (either coding or non-coding RNA) via RISC, or alternately, translational inhibition as is known in the art. In another embodiment, modulation of gene expression by siNA molecules of the invention can result from transcriptional inhibition (see for example Janowski et al., 2005, *Nature Chemical Biology,* 1:216).

RNA interference (RNAi) is a process by which double-stranded RNA (dsRNA) is used to silence gene expression. Without being bound to any particular theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

In an embodiment, the above-mentioned inhibition is with a short hairpin RNA (shRNA) or a small interfering RNA (siRNA). In a further embodiment, the above-mentioned inhibition is with a short hairpin RNA (shRNA).

Short hairpin interfering RNA (shRNA) as used herein refers to a molecule (e.g., a single oligonucleotide chain) that comprises both the sense and antisense strands of an interfering RNA in a stem-loop or hairpin structure (e.g., a shRNA). For example and as used in the studies described herein, shRNAs can be expressed from DNA vectors (e.g., a lentiviral vector) in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

In an embodiment, the shRNA molecules of the invention are about 15 to about 100 nucleotides in length. In a further embodiment, the shRNA molecules of the invention are about 35 to about 65 (e.g., about 35, 40, 45, 50, 55, 60 or 65) nucleotides in length. In a further embodiment, the shRNA molecules are about 38 to about 44 (e.g., about 38, 39, 40, 41, 42, 43, or 44) nucleotides in length and comprises about 15 to about 25 (e.g., about 15, 16, 17, 18, 19, 20, 21, 22, 23, 24, or 25) base pairs.

In an embodiment, the above-mentioned shRNA is encoded by a nucleic acid comprising the following nucleotide sequence: AAAGGGAGACTCTATTTAAGATTAGTGAAGCCACAGATGTAATCTTAAATA-GAGTCTCCCTTC (SEQ ID NO: 3). In a further embodiment, the above-mentioned shRNA is encoded by a nucleic acid comprising the following nucleotide sequence: TGCTGTTGACAGTGAGCGAAAGG-GAGACTCTATTTAAGATTAGTGAAGCCA-CAGATGTAATCTTAAATAGAGTCTCCCT-TCTGCCTACTGCCTCGGA (SEQ ID NO: 4).

In an embodiment, the above-mentioned shRNA is comprised in a vector (e.g., an expression vector). In an embodiment, the above-mentioned shRNA is operatively linked to a transcriptional regulatory sequence in said vector. In a further embodiment, the above-mentioned vector is a viral vector (e.g., a lentiviral vector, an adenoviral vector, and adeno-associated virus vector, a herpes virus vector, a vaccinia virus vector). Methods for cloning and expressing shRNA in expression vectors are well known in the art (see, for example, McIntyre and Fanning, 2006. *BMC Biotechnol.* 6: 1). In an embodiment, the above-mentioned vector is suitable for delivering the above-mentioned shRNA into a muscle cell (e.g., a myoblast). Vector and methods for delivering shRNA and/or siRNA into muscle cells are well known in the art (see, for example, Herndon and Fromm, *J Muscle Res Cell Motil.* 28: 11-17; Hu et al., *Biochem Biophys Res Commun.* 343: 1038-44; U.S. Pat. No. 7,235,233).

In another aspect, the present invention provides a host cell (e.g., a muscle cell, a myoblast) comprising the above-mentioned shRNA or vector (e.g., transfected or transformed with the shRNA or vector). A host cell comprising the above-mentioned shRNA or vector may be implanted/transplanted in a subject in need thereof for inhibiting PGE$_2$ biosynthesis and/or activity in a cell (e.g., a muscle cell and/or a muscle cell precursor) from said subject, thereby preventing and/or treating cDM1 in the subject. The invention further provides a composition comprising the above-noted cell and a suitable carrier/excipient, such as a pharmaceutically acceptable or biocompatible carrier/excipient. In an embodiment, the carrier/excipient is adapted for administration (e.g., implantation, transplantation or transfer) of said cell into a subject. The invention further provides a package comprising the above-noted cell together with instructions for preventing/or treating cDM1 in a subject. The invention further provides a use of the cell for preventing/or treating cDM1 in a subject, or for the preparation of a medicament for preventing/or treating cDM1 in a subject. The invention further provides a composition for preventing/or treating cDM1 in a subject, comprising the above-noted cell and a suitable carrier/excipient.

For the method or use of the present invention, the above-mentioned inhibitor/agent may conveniently be presented as a pharmaceutical composition with a pharmaceutically acceptable carrier or excipient. As used herein "pharmaceutically acceptable carrier" or "excipient" includes any and all solvents, dispersion media, coatings, antibacterial and antifungal agents, isotonic and absorption delaying agents and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art (see, for example, Rowe et al., Handbook of pharmaceutical excipients, 2003, 4$^{th}$ edition, Pharmaceutical Press, London UK).

In an embodiment, the above-mentioned composition and carrier/excipient are suitable for intramuscular administration.

In an embodiment, such compositions include the agent, in a therapeutically or prophylactically effective amount sufficient to prevent and/or treat cDM1, and a pharmaceutically acceptable carrier. A "therapeutically effective amount" refers to an amount effective, at dosages and for periods of time necessary, to achieve the desired therapeutic result, such as an amelioration of symptoms of cDM1 or increased survival time of the affected animal. A therapeutically effective amount of an agent capable of inhibiting the biosynthesis or activity of prostaglandin E$_2$ (PGE$_2$) may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result, such as preventing or inhibiting onset of cDM1. A prophylactically effective amount can be determined as described above for the therapeutically effective amount. For any particular subject, specific dosage regimens may be adjusted over time according to the individual need and the professional judgement of the person administering or supervising the administration of the compositions.

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in PGE$_2$ activity and/or levels in a muscle cell, a decrease/reduction in COX activity and/or levels in a muscle cell, an increased in myoblast differentiation/fusion, an amelioration of symptoms of cDM1, and increased survival time of the affected host animal, following administration of the inhibitor of the biosynthesis or activity of prostaglandin E$_2$ (PGE$_2$). In embodiments, the decrease in PGE$_2$ activity and/or levels may be, for example, at least 10%, at least 20%, at least 30%, at least 40%, at least 50%, at least 60%, at least 70%, at least 80%, at least 90%, at least 95%, at least 98%, at least 99% or 100% (i.e., complete inhibition of PGE$_2$ level or activity) decrease in PGE$_2$ expression or levels in a muscle cell (e.g., myoblast). In embodiments, the decrease in COX (e.g., COX-2) activity and/or expression may be, for example, at least 10%, at least 20%, at least 30%, at least 40%, at least 50%, at least 60%, at least 70%, at least 80%, at least 90%, at least 95%, at least 98%, at least 99% or 100% (i.e., complete inhibition of COX expression or activity) in a muscle cell (e.g., myoblast). In embodiments, the increase in muscle cell (e.g., myoblast) differentiation/fusion may be, for example, at least 10%, at least 20%, at least 30%, at least 40%, at least 50%, at least 60%, at least 70%, at least 80%, at least 90%, at least 95%, at least 100% (2-fold). In accordance with the invention, a prophylactic effect may comprise a decrease in the onset of or of the severity of cDM1, symptoms and related effects, and increased survival time of the affected host animal, following administration of an inhibitor of the biosynthesis or activity of PGE$_2$.

In an embodiment, the above-mentioned inhibition is mediated by a combination of at least two active/therapeutic agents. Thus, the pharmaceutical compounds of the present invention may be administered alone or in combination with other active agents useful for the treatment, prophylaxis or amelioration of symptoms of cDM1. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time.

In an embodiment, an agent of the invention is administered such that it comes into contact with a muscle cell and/or a muscle cell precursor (e.g., a myoblast) of said subject. For example, the agent may be directly injected into a muscle. Alternatively, the agent can be administered systemically (e.g., intravenously, or orally) in a form capable of delivering the agent into a muscle cell and/or a muscle cell precursor.

In another aspect, the present invention provides a kit or package comprising at least one of the above-mentioned agent/inhibitor (or a pharmaceutical composition comprising the agent/inhibitor) together with instructions for its use for the prevention and/or treatment of cDM1 in a subject. The kit may further comprises, for example, containers, buffers, a device (e.g., syringe) for administering the agent/inhibitor.

In another aspect, the present invention provides a method for prognosticating or diagnosing cDM1 is a first subject, said method comprising determining a test level of expression or activity of (i) PGE$_2$, (ii) a mediator involved in PGE$_2$ biosynthesis, or (iii) both (i) and (ii) in a biological sample from said first subject, wherein an increase in the test level or activity relative to a corresponding reference level or activity is indicative that the first subject suffers from cDM1 or is at risk of suffering from cDM1.

In the methods of the invention, the test level or activity of (i) PGE$_2$, (ii) a mediator involved in PGE$_2$ biosynthesis, or (iii) both (i) and (ii) may be compared to a corresponding "reference" level or activity in order to diagnose/prognose cDM1 in a subject, or assess the risk that the subject will develop cDM1.

Such a reference level or activity may for example be established by determining (i) the level or activity of $PGE_2$ and/or of a mediator involved in $PGE_2$ biosynthesis in biological samples obtained from one or more healthy/normal subject(s) (i.e., subject(s) known to not be afflicted by, or not at risk of developing cDM1). Such a "reference level or activity" may refer to the level or activity of $PGE_2$ and/or of a mediator involved in $PGE_2$ biosynthesis measured in a "control" sample that contains a known level or activity that closely reflects the average level or activity in an average healthy/normal subject (typically an age- and gender-matched healthy subject), as described above.

In an embodiment, the above-mentioned reference level or activity is the level or activity of (i) $PGE_2$, (ii) a mediator involved in $PGE_2$ biosynthesis, or (iii) both (i) and (ii) in a corresponding biological sample from a second subject not suffering from, or not at risk of developing, cDM1, and wherein a higher level of expression or activity in the sample from said first subject relative to the level in the sample from said second subject is indicative that said first subject has or is at risk of developing cDM1.

In a further embodiment, the above-mentioned reference level or activity is a corresponding level or activity of (i) $PGE_2$, (ii) a mediator involved in $PGE_2$ biosynthesis, or (iii) both (i) and (ii) in a corresponding biological sample obtained from the first subject at an earlier time, i.e. prior to obtaining the sample in which the test level or activity is determined. Changes in the level or activity of (i), (il) or both (i) and (ii) above, in the same subject over time may be used for prognostication of cDM1. For example, a decrease in the level or activity of (i), (ii) or both (i) and (ii) above over time is indicative of an amelioration of the cDM1 conditions in the subject (i.e., improved health), whereas an increase is indicative of poorer cDM1 conditions (i.e., poorer health).

In an embodiment, the above-mentioned test level or activity in the sample from said first subject is at least 20% higher, in a further embodiment at least 30%, in a further embodiment at least 40%, in a further embodiment at least 50%, in a further embodiment at least 100% (i.e. 2-fold), in a further embodiment at least 4-fold, in a further embodiment at least 10-fold, than the reference level or activity.

Alternatively, such a reference level or activity may be established by determining the level or activity of $PGE_2$ and/or of a mediator involved in $PGE_2$ biosynthesis in biological samples obtained from one or more cDM1 subject(s) (i.e., subject(s) suffering from, or at risk of developing cDM1). Such "reference level or activity" may refer to the level or activity of $PGE_2$ and/or of a mediator involved in $PGE_2$ biosynthesis measured in a "control" sample that contains a known level or activity that closely reflects the average level or activity in an average cDM1 subject, as described above.

In an embodiment, the above-mentioned reference level or activity is the level or activity of (i) $PGE_2$, (ii) a mediator involved in $PGE_2$ biosynthesis, or (iii) both (i) and (ii) in a corresponding biological sample from a second subject suffering from cDM1, and wherein a substantially similar expression or activity in the sample from said first subject relative to the level or activity in the sample from said second subject is indicative that said first subject has or is at risk of developing cDM1. In an embodiment, "substantially similar" refers to a level or activity that differs by less than 20%, in a further embodiment by 15% or less, in a further embodiment by 10% or less, in a further embodiment by 5% or less, relative to the reference level or activity.

Methods for determining the level or activity of $PGE_2$ are well known in the art. Examples include high-pressure liquid chromatography (HPLC), gas chromatography mass spectrometry (GC-MS) enzyme-linked immunosorbent assay (ELISA), also known as enzyme immunoassay (EIA), radio-immunoassay (RIAs), fluorescence polarization (FP), and scintillation proximity assay (SPA). The level and/or activity $PGE_2$ can be assessed for example using commercially available kits (e.g., Prostaglandin $E_2$ EIA kit—monoclonal, and Prostaglandin $E_2$ Quant-PAK from Cayman Chemical; Flash Plate® Prostaglandin $E_2$ Assay System from PerkinElmer™; HTRFT™ $PGE_2$ assay from Cisbio). In an embodiment, $PGE_2$ level or activity is measured by ELISA. In an embodiment, $PGE_2$ level or activity is measured using the method described in Example 1 below.

Methods for determining the level or activity of a mediator involved in $PGE_2$ biosynthesis are well known in the art. For example, methods for determining the activity of COX-2 are described in Yu et al., 1997. *J. Biol. Chem.* 272:21181-21186, U.S. Pat. No. 5,543,297, U.S. Pat. No. 5,475,021, U.S. Pat. No. 6,045,773 and U.S. Pat. No. 7,189,504; methods for determining the activity of mPGES are described in US Patent publication No. 2004/0082021.

Expression levels may in general be detected by either detecting mRNA from the cells and/or detecting expression products, such as polypeptides and proteins. Expression of a polypeptide involved in $PGE_2$ biosynthesis (e.g. COX-2), and/or of a nucleic acid encoding a polypeptide involved in $PGE_2$ biosynthesis (e.g., a nucleic acid encoding COX-2), may be measured by any of a variety of known methods in the art. In general, the nucleic acid sequence of a nucleic acid molecule (e.g., DNA or RNA) in a subject sample can be detected by any suitable method or technique of measuring or detecting gene sequence or expression. Such methods include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level.

Expression levels may be represented by any form of data which is suitable for use in the methods (e.g., comparisons and assessments) described herein. In embodiments, such data may be recorded on a computer-readable medium.

Methods to measure protein expression levels of selected genes of this invention are well known in the art. Examples of such methods include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the protein including but not limited to DNA binding, ligand binding, interaction with other protein partners, as well as assays to assess enzymatic activity.

Methods for normalizing the level of expression of a gene are well known in the art. For example, the expression level of a gene of the present invention can be normalized on the basis of the relative ratio of the mRNA level of this gene to the mRNA level of a housekeeping gene or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the ACTIN gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene® QPCR Human Reference Total RNA, Clontech™ Universal Reference Total RNA, and XpressRef™ Universal Reference Total RNA.

Nucleic acid arrays may be useful for detecting the level of expression of a nucleic acid encoding a polypeptide involved in $PGE_2$ biosynthesis. The production and application of high-density arrays in gene expression monitoring have been disclosed previously in, for example, PCT Publication No. WO 97/10365; PCT Publication No. WO 92/10588; U.S. Pat. No. 6,040,138; U.S. Pat. No. 5,445,934; or PCT Publication No. WO 95/35505, all of which are incorporated herein by reference in their entireties. Also for examples of arrays, see Hacia et al., *Nature Genetics* 14:441; Lockhart et al., *Nat. Biotechnol.* 14:1675-1680; and De Risi et al., *Nature Genetics* 14:457, each of which is incorporated by reference in its entirety. In general, in an array, an oligonucleotide, a cDNA, or genomic DNA, that is a portion of a known gene, occupies a known location on a substrate. A nucleic acid target sample is hybridized with an array of such oligonucleotides and then the amount of target nucleic acids hybridized to each probe in the array is quantified. Quantification may be achieved for example using a confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used. In a particularly preferred embodiment, one can use the knowledge of the genes described herein to design novel arrays of polynucleotides, cDNAs or genomic DNAs for screening methods described herein. Such novel pluralities of polynucleotides are contemplated to be a part of the present invention and are described in detail below.

Suitable nucleic acid samples for screening on an array contain transcripts of interest or nucleic acids derived from the transcripts of interest (i.e., transcripts encoding one or more polypeptide(s) involved in $PGE_2$ biosynthesis). As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, fragments thereof, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, fragments thereof, and the like. Preferably, such a sample is a total RNA preparation of a biological sample (e.g., muscle cell sample, myoblast sample). More preferably in some embodiments, such a nucleic acid sample is the total mRNA isolated from such a biological sample.

Methods of isolating total mRNA are well known to those of skill in the art. In one embodiment, the total nucleic acid is isolated from a given sample using, for example, an acid guanidinium-phenol-chloroform extraction method and polyA and mRNA is isolated by oligo dT column chromatography or by using $(dT)_n$ magnetic beads (see, e.g., Sambrook et al., Molecular Cloning: A Laboratory Manual ($2^{nd}$ ed.), Vols. 1-3, Cold Spring Harbor Laboratory, (1989), or Current Protocols in Molecular Biology, F. Ausubel et al., ad. Greene Publishing and Wiley-Interscience, New York (1987)).

In an embodiment, the above-mentioned mediator involved in $PGE_2$ biosynthesis is mPGES-1. In a further embodiment, the above-mentioned method comprises determining the level or activity of a polypeptide comprising the sequence of SEQ ID NO: 6, or the level of a nucleic acid encoding a polypeptide comprising the sequence of SEQ ID NO: 6 (e.g., the nucleic acid comprising the sequence of SEQ ID NO: 5, or a fragment thereof).

In another embodiment, the above-mentioned mediator involved in $PGE_2$ biosynthesis is COX-2 (also known as prostaglandin-endoperoxide synthase 2, PTGS2). In a further embodiment, the above-mentioned method comprises determining the level or activity of a polypeptide comprising residues 18-604 of the sequence of SEQ ID NO: 12 (mature COX-2 polypeptide), or a fragment thereof, or the level of a nucleic acid encoding a polypeptide comprising residues 18-604 of the sequence of SEQ ID NO: 12 (e.g., the nucleic acid comprising the sequence of SEQ ID NO: 11), or a fragment thereof.

In another aspect, the present invention provides a method for identifying a compound, or determining whether a test compound is useful, for preventing and/or treating cDM1, said method comprising determining the level and/or activity of (i) $PGE_2$, (ii) a mediator involved in $PGE_2$ biosynthesis, or (iii) both (i) and (ii), in a cell comprising (i) $PGE_2$, (ii) a mediator involved in $PGE_2$ biosynthesis, or (iii) both (i) and (ii), and/or $PGE_2$ biosynthetic activity; wherein a decrease in the level and/or activity in the presence relative to the absence of said test compound is indicative that said test compound is useful for preventing and/or treating cDM1.

In another aspect, the present invention provides a method for determining whether a test compound is useful for preventing and/or treating cDM1, said method comprising contacting said test compound with a biological sample from a subject at risk of or suffering from cDM1, a cell comprising (i) $PGE_2$, (ii) a mediator involved in $PGE_2$ biosynthesis, or (iii) both (i) and (ii), and/or a mediator involved in $PGE_2$ biosynthesis; and determining the level and/or activity of (i) $PGE_2$, (ii) a mediator involved in $PGE_2$ biosynthesis, or (iii) both (i) and (ii); wherein a decrease in the level and/or activity in the presence relative to the absence of said test compound is indicative that said test compound is useful for preventing and/or treating cDM1.

In embodiments, other methods of determining the effect of a test compound on the level and/or activity of (i) $PGE_2$, (ii) a mediator involved in $PGE_2$ biosynthesis, or (iii) both (i) and (ii) may be utilized in the methods of the invention, such as determining whether a test compound modulates binding of (i) $PGE_2$, (ii) a mediator involved in $PGE_2$ biosynthesis, or (iii) both (i) and (ii) to one or more of its corresponding receptor(s) or effector molecule(s).

In an embodiment, the above-mentioned method further comprises: (a) contacting a myoblast sample from a subject at risk of or suffering from cDM1 with said test compound; (b) culturing said myoblasts under conditions suitable for myoblast fusion or differentiation; (c) determining the level of fusion or differentiation of said myoblast; wherein an increase in the level of fusion or differentiation of said myoblasts in the presence relative to the absence of said test compound is indicative that said test compound is useful for preventing and/or treating cDM1.

In an embodiment, the above-mentioned level of fusion or differentiation is determined by measuring the index of fusion of said myoblasts after said culturing (e.g. using the method described in Example 1 below). In another embodiment, the above-mentioned conditions suitable for myoblast fusion or differentiation are the conditions described in Example 1 below.

In another embodiment of the invention, a reporter assay-based method of selecting agents which modulate expression of a mediator involved in $PGE_2$ biosynthesis is provided. The method includes providing a cell comprising a nucleic acid sequence comprising a transcriptional regulatory sequence of a mediator involved in $PGE_2$ biosynthesis, operably-linked to a suitable reporter gene. The cell is then exposed to the agent suspected of affecting expression of a mediator involved in $PGE_2$ biosynthesis (e.g., a test compound) and the transcription efficiency is measured by the expression and/or activity of the reporter gene. The expression and/or activity can then be compared to the expression and/or activity of the reporter gene in cells unexposed to the agent in question. Suitable reporter genes include but are not limited to beta-D galactosidase, luciferase, chloramphenicol acetyltransferase and fluorescent green protein.

Accordingly, the present invention further provides a method of identifying or characterizing a compound for preventing and/or treating cDM1, said method comprising: (a) contacting a test compound with a cell comprising a first nucleic acid comprising a transcriptionally regulatory element normally associated with a gene encoding a mediator involved in $PGE_2$ biosynthesis (e.g., a promoter region naturally associated with a PGE synthase gene [e.g., mPGES-1 or -2] or COX gene [e.g., COX-1 or COX-2]) operably linked to a second nucleic acid comprising a reporter gene capable of encoding a reporter protein; and (b) determining reporter gene expression or reporter protein activity; wherein a decrease in reporter gene expression or reporter protein activity in the presence relative to in the absence of the test compound is indicative that the test compound may be used for for preventing and/or treating cDM1.

The above-noted assays may be applied to a single test compound or to a plurality or "library" of such compounds (e.g., a combinatorial library). Any such compounds may be utilized as lead compounds and further modified to improve their therapeutic, prophylactic and/or pharmacological properties preventing and/or treating cDM1.

Such assay systems may comprise a variety of means to enable and optimize useful assay conditions. Such means may include but are not limited to: suitable buffer solutions, for example, for the control of pH and ionic strength and to provide any necessary components for optimal activity and stability (e.g., protease inhibitors), temperature control means for optimal activity and or stability, of the mediator involved in $PGE_2$ biosynthesis, and detection means to enable the detection of its activity. A variety of such detection means may be used, including but not limited to one or a combination of the following: radiolabelling, antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

The assay may be carried out in vitro utilizing a source of a mediator involved in $PGE_2$ biosynthesis which may comprise a naturally isolated or recombinantly produced mediator involved in $PGE_2$ biosynthesis, in preparations ranging from crude to pure. Such assays may be performed in an array format. In certain embodiments, one or a plurality of the assay steps are automated.

A homolog, variant and/or fragment of a mediator involved in $PGE_2$ biosynthesis which retains activity may also be used in the methods of the invention.

"Homology", "homologous" and "homolog" refer to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to or is a "homolog" of another sequence if the two sequences are substantially identical and the functional activity of the sequences is conserved (as used herein, the term 'homologous' does not infer evolutionary relatedness). Two nucleic acids or amino acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%, e.g., with any of the sequences described herein. As used herein, a given percentage of homology between sequences denotes the degree of sequence identity in optimally aligned sequences. An "unrelated" or "non-homologous" sequence shares less than 40% identity, though preferably less than about 25% identity, with any of the sequences described herein.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%, e.g., with any of the sequences described herein. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, more preferably highly stringent conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

In another aspect, the present invention also features kits for prognosticating/diagnosing cDM1 in a subject, or for assessing a subject's risk for developing cDM1. The kits may include suitable means, e.g., reagents, for evaluating the level or activity of $PGE_2$, and/or the level or activity of a mediator that play a role in $PGE_2$ biosynthesis. In an embodiment, the above-mentioned mediator is a polypeptide (i.e. an enzyme) and its level of expression may be measured at the nucleic acid (e.g., mRNAs) or protein level. Kits for evaluating expression of nucleic acids can include, for example, probes or primers that specifically bind a nucleic acid of interest (e.g., a nucleic acid, the expression of which correlates with the disease (cDM1) or with increased risk of developing cDM1). The kits for evaluating nucleic acid expression can provide substances useful as reference/standard (e.g., a sample containing a known quantity of a nucleic acid to which test results can be compared, with which one can assess factors that may alter the readout of a diagnostic test, such as variations in an enzyme activity or binding conditions). Kits for assessing nucleic acid expression can further include other reagents useful in assessing levels of expression of a nucleic acid (e.g., buffers and other reagents for performing amplification reactions, or for detecting binding of a probe to a nucleic acid). In addition to, or as an alternative, kits can include reagents for detecting proteins (e.g., antibodies or antigen-binding fragments thereof) and/or reagents for measuring the activity (e.g. enzymatic activity) of the proteins. The kits may also provide instructions for performing the assay used to evaluate the level or activity and/or instructions for determining risk based on the results of the assay. For example, the instructions can indicate that the levels or activity of $PGE_2$, or of a mediator involved in its biosynthesis (e.g., relative to a standard or a control), correlate with the presence of the disease (cDM1) in the subject, or with an increased risk for developing the disease. Kits can also provide instructions, containers, computer readable media (comprising, for example, a data analysis program, a reference level or activity, etc.), control samples, and other reagents for obtaining and processing samples for analysis.

In general, typical biological samples include, but are not limited to, sputum, serum, lymphatic fluid, blood, blood cells (e.g., peripheral blood mononuclear cells), tissue or fine needle biopsy samples, urine, peritoneal fluid, colostrums, breast milk, fetal fluid, tears, and pleural fluid, or cells therefrom. In an embodiment, the above-mentioned biological sample is a muscle cell or a muscle cell precursor sample (e.g., a myoblast). In another embodiment, the above-mentioned biological sample is a myoblast cell sample. In another embodiment, the above-mentioned biological sample is a cell line derived/generated from the above-mentioned muscle cell or muscle cell precursor.

In an embodiment, the above-mentioned inhibition or inhibitor is selective for $PGE_2$, i.e., results in inhibition of $PGE_2$ to a greater extent relative to another prostaglandin or without substantial inhibition of another prostaglandin.

In an embodiment, the above-mentioned subject is a mammal. In a further embodiment, the above-mentioned mammal is a human.

The present invention is illustrated in further details by the following non-limiting examples.

Example 1

Materials and Methods

Figure 15:
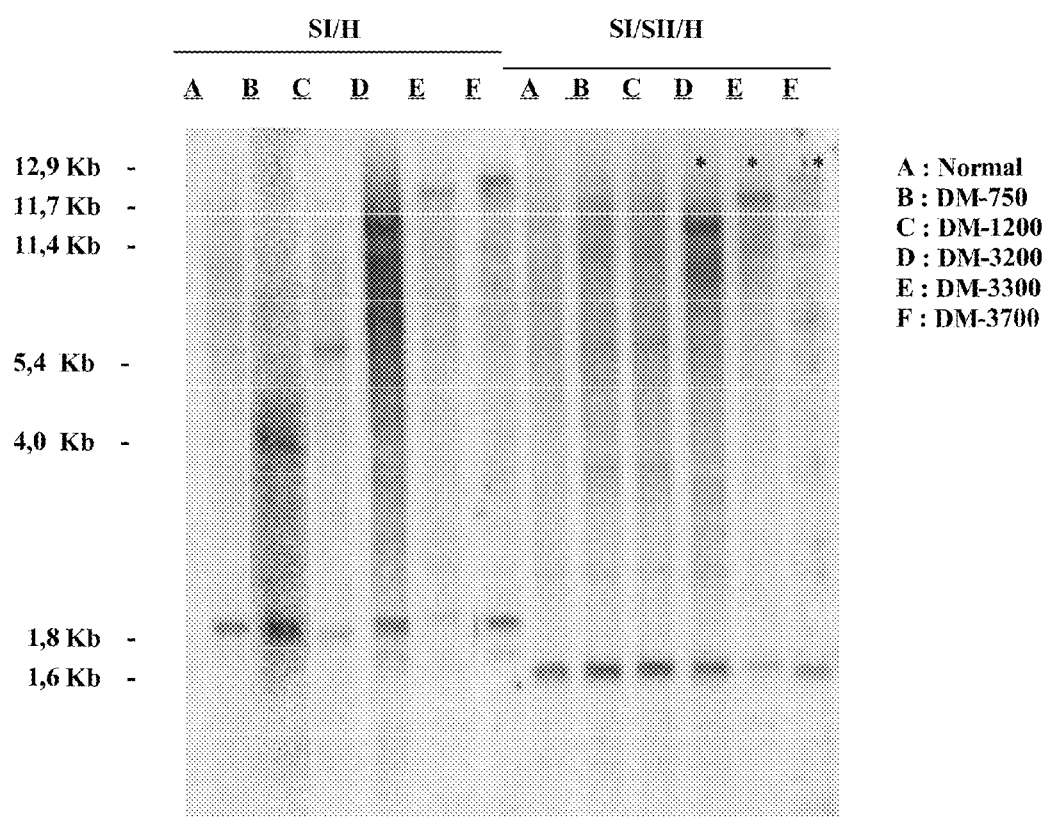
FIG. 15 shows a Southern blot analysis of DNAs from normal (A), DM-750 (B), DM-1200 (C), DM-3200 (D), DM-3300 (E) and DM-3700 (F) cells. Genomic DNA prepared form the various cells was digested using SacI and HindIII with or without the methylation-sensitive restriction enzyme SacII and a Southern blot was performed as previously described (Steinbach et al., 1998. *Am J Hum Genet.* 62(2): 278-85). Restriction enzymes used for genomic DNA digestions are the following: SacI (SI), SacII (SII) and HindIII (H). The asterisk (*) indicates the DNA fragment containing the aberrantly methylated downstream SacII site in DM-3200, DM-3300 and DM-3700 myoblasts. Bands at 4.0 kb, 5.4 and 11.4 kb represent full-length (SacI to HindIII) mutant transcripts of DM-750, DM-1200, DM-3200, DM-3300 and DM-3700 myoblasts, respectively. Bands at 1.8 kb represent the full-length normal transcripts in all myoblasts.

Primary human myoblast culture. Normal human myoblasts were derived from a 12-week-old fetus. DM-750, DM-1200 and DM-3200 myoblasts were obtained from the skeletal muscles of 20-, 13- and 15-week-old DM1 fetuses. The length of the CTG repeat expansion in these myoblasts was approximately 750, 1200 and 3200 CTG repeats, respectively, as determined by Southern blot (FIG. 15). Because these myoblasts were obtained from aborted fetuses, it was not determined if they had DM1 or cDM1. All biopsies were obtained in accordance with the Laval University Medical Research Centre ethical committees. Myoblasts were grown in MCDB 120 medium (JRH Biologicals, Lenexa, Kans.) supplemented with 15% heat-inactivated fetal bovine serum, 5 mg/ml insulin, 0.5 mg/ml BSA, 10 ng/ml epidermal growth factor, 0.39 mg/ml dexamethasone, 50 mg/ml streptomycin and 50 mg/ml penicillin (proliferative medium), as previously described (Langlois et al., 2003 *Mol. Ther.* 7: 670-680; Furling D et al., 2001. *Neuromuscul Disord.* 11: 728-35). For myoblast differentiation, cells were subsequently cultured in DMEM supplemented with 0.5% heat-inactivated fetal bovine serum, 10 mg/ml insulin, 10 mg/ml apo-transferrin, 50 mg/ml streptomycin and 50 mg/ml penicillin (differentiating medium). All cultures were incubated at 37° C. in a humid atmosphere containing 5% $CO_2$. Normal and DM cells were used between the $4^{th}$ and $6^{th}$ passage. The number of passages refers to the total number of passages from the time following the isolation of the initial myoblast population.

Co-cultures. Normal human myoblasts were transduced with pHIV7/eGFP viral vector. About 100% of the cells expressed eGFP and no further cell purification was necessary. Co-cultures were initiated with eGFP-positive normal myoblasts mixed with either human cDM1 or control myoblasts (50/50). At 90% confluence, cells were shifted to the differentiating medium for 4 days. The index of fusion was determined by counting the number of nuclei in multinucleated GFP-positive cells and was expressed as a percentage of the total number of nuclei in GFP-positive cells.

Preparation of conditioned medium. Conditioned media (CM) were prepared from normal myoblasts and DM1 myoblasts with 750, 1200 and 3200 repeats. At 70% confluence, cells were washed with HBSS for one hour to remove residual serum and were grown in a proliferative medium containing 15% FBS and recombinant epidermal growth factor (rEGF) for 2 days. The medium was then collected and frozen until use. Cells were washed with HBSS and were further grown in serum-free proliferative medium (MCBD 120-serum free medium) for 2 days. The medium was then collected and frozen until use. This medium was used for the growth of myoblasts during differentiation. Conditioned medium made in proliferative medium containing serum was added to myoblasts at 70% confluence. Two days later (90% confluence), the cells were switched in MCDB 120-serum-free CM and were further grown in this medium for the next four days. CM was renewed every day. Unconditioned serum and serum-free proliferative medium were used as control.

Fractioning of conditioned medium. Conditioned medium was prepared from DM1 myoblasts with 3200 repeats and normal myoblasts as described above. Conditioned media prepared with and without serum were fractionated on Amicon Ultra-15 Centrifugal Devices with 30 kDa of nominal molecular weight limit (Millipore, USA). Unconditionated proliferative and differentiating medium were also fractionated in a similar way. CM containing proteins with a molecular weight (MW) below 30 kDa was supplemented with fractionated unconditionated media containing proteins with MW above 30 kDa. CM containing proteins with a MW above 30 kDa was supplemented with fractionated unconditionated media containing proteins with MW below 30 kDa. The fractioned CM was added to normal myoblasts when they reached 70% confluence. At confluence, the serum-free fractioned medium was added to the cells to induce differentiation. The Index of Fusion was determined after 4 days of differentiation. The index of fusion was determined by counting the number of nuclei in multinucleated cells and was expressed as a percentage of the total number of nuclei.

Western blot analysis. Cells were scraped after 4 days of differentiation. The complete procedure for the extraction of cytoplasmic and nuclear proteins used was described previously (Jansen et al., 1996. *Nat Genet.* 13: 316-324). Electrophoresis samples were prepared by solubilizating in Laemmli's buffer and boiling for 5 min. Proteins (20 µg) were separated by SDS-PAGE using a 10% polyacrylamide resolving gel slab and were transferred to PVDF membranes (BioTrace, Pall Coproration). After blocking non-specific sites, membranes were incubated with primary antibodies: anti-myogenin (Clone F5D, DSHB, Iowa), anti-myoD (BD PharMingen), anti-p21 (Bio/Can Scientific), anti-COX-2 (obtained from Dr Michel A. Fortier, CHUL, Quebec), anti-β-actin (Bethyl Lab). Membranes were washed, and incubated with an anti-immunoglobulins antibody horseradish peroxidase-conjugated. Immune complexes were detected using an enhanced chemioluminescence kit (ECL, Amersham).

Southern blot. Genomic DNA was extracted by using proteinase K combined with denaturing ability of the ionic detergent SDS, as previously described (Gross-Bellard et al., 1973. *Eur J Biochem* 36: 32-38). Twelve mg genomic DNA was used in every digestion with appropriate restriction enzymes and samples were purified by phenol-chloroform extraction prior to gel loading. DNA was resolved on a 0.8% agarose gel, blotted onto a Biodyne B nylon membrane and hybridized with the $^{32}$P-labelled DMPK probe according to standard procedures.

Inhibition of mPGES-1 by shRNA. 293T cells were transfected in 100 mm petri dishes with 10 µg of DNA using calcium phosphate. The DNA transfected comprised: 5.2 µg of Lentiviral vector (Open Biosystems, Clone ID: V2LHS_67663, Cat No. RHS4430-98484755); 3.2 µg of pCHGP-2 vector; 0.9 µg of pCMV-Rev and 1.2 µg of pCMV-VSVG. The supernatants were collected 36 to 48 hours after transfection and kept frozen at −80° C. until use. Before use, the viral supernatants were thawed and supplemented with polybren (8 µg/ml). Myoblasts were seeded in 15 mm wells and cultured in MB-1 medium supplemented with 15% FBS. At 40-50% confluence, myoblasts were washed three times with sterile 1× PBS. Cells were the incubated overnight with about 500 µl of the viral supernatant (to completely cover the cells). After incubation, the viral supernatant was removed and the cells were cultured in proliferation medium (MB-1 medium supplemented with 15% FBS and rEGF). When the cells reached confluence, they were transferred in the differentiation medium (DMEM high glucose supplemented with 0.5% FBS, insulin and apotransferin) and incubated for three days to induce differentiation. After this 3-day incubation, cells were fixed using 4% paraformaldehyde and stained using 100 ng/ml DAPI. mPGES mRNAs were quantified by RT-PCR. Total RNA was extracted using Trizol™ reagent (Life Technologies) according to the manufacturer's specifications. First strand cDNA synthesis and PCR amplifications of the mPGES-1 and β-actin DNAs were done using the following primers: mPGES-1: Forward primer; GAAGAAGGC-CTTTGCCAAC (SEQ ID NO: 7); reverse primer; GGGT-TAGGACCCAGAAAGGA (SEQ ID NO: 8); β-actin: Forward: GCGGGAAATCGTGCGTGACATT (SEQ ID NO: 9), Reverse primer; GATGGAGTTGAAGGTAGTTTCGTG (SEQ ID NO: 10)) and PCR assays were performed in the linear range of the amplifications for both mPGES-1 and β-actin, which is around 35 cycles under the experimental conditions described herein. PCR products were resolved on a 2.5% agarose gel and densitometry analysis was performed using an AlphaImager™ imaging system and software (Innotech. Corp.).

Determination of $PGE_2$ and $PGF_2$-alpha concentration in conditioned medium. cDM1 and DM1 myoblasts were cultured (100 mm Petri dishes) in MB-1 medium supplemented with 15% FBS and rEGF. At 75-80% confluence, cells were transferred in MB-1 medium only and incubated for 48 hours. After incubation, the supernatants were collected and the concentration of $PGE_2$ and $PGF_2$-alpha was measured by ELISA as described previously (Chapdelaine et al., 2006. *Mol. Hum. Reprod.* 12: 309-319; Asselin et al., 1996. *Biol. Reprod.* 54: 371-379). The inter- and intra-assay coefficient of variations (n=12) were 16 and 10%, respectively.

Determination of COX-2 expression by myoblasts. For "in vitro" expression, DM1 cell lines were cultured in MB-1 medium supplemented with 15% FBS and rEGF in 24-well plates (15 mm wells). At 70-80% confluence, cells were trypsinized using Trypsin-EDTA (0.25%, 1 mM) (Invitrogen, Cat. No. 25200072). Cells were then collected by centrifugation, and lysed using 50 μl of the following lysis buffer: 20 mM Tris-Hcl, pH 7.5, 1 mM DTT, 1 mM PMSF and 1% SDS. Cells were sonicated (3 times×20 sec., at 30 sec. intervals). The mixture was centrifugated to remove cell debris, and the total protein concentration in the supernatant was measured using Amido-Black 10B (Bio-Rad, Cat. No. 161-0402) according to the manufacturer's protocol. Supernatant samples were aliquoted (20 μg of total protein/aliquot) and stored at −20° C.

For "in vivo" expression, 50-100 mg of muscular biopsies was homogenized in 500 μl of the lysis buffer described above. Cells were sonicated (3 times×20 sec., at 30 sec. intervals). The mixture was then centrifugated to remove cell debris, and the total protein concentration in the supernatant was measured using Amido-Black 10B (Bio-Rad, Cat. No. 161-0402) according to the manufacturer's protocol. Supernatant samples were aliquoted (20 μg of total protein/aliquot) and stored at −20° C.

Following addition of migration buffer (5× migration buffer=1.25 ml Tris-HCl 0.5 M, pH 6.8; 2.5 ml glycerol; 0.75 g. SDS; 0.5 ml β-Mercaptoethanl, 2.5 mg Bromophenol Blue; complete to 10 ml with water), aliquots were migrated on a 10% acrylamide SDS-PAGE gel. Following migration, samples were transferred on a PVDF membrane (Millipore, Cat. No. CA28148-752). The membranes were blotted using a rabbit anti-human COX-2, followed by detection with an HRP-conjugated, anti-rabbit secondary antibody. The intensity of the signal was then assessed using the AlphaImager™ software.

Effect of $PGE_2$ and $PGF_2$-alpha on myoblast fusion. $PGE_2$ and $PGF_2$-α were purchased from Sigma (Cat. No. PO409-1 mg et P5069-1MG). 10 mM of $PGE_2$ or $PGF_2$-α were added to proliferative medium (MB-1+15% FBS+rEGF) 2 days before confluence. At confluence, the same amount of $PGE_2$ or $PGF_2$-α was added to the differentiating medium (DMEM+0.5% FBS+insulin+apotransferin). The index of fusion was determined 3 days later.

Effect of Aspirin™ on the production of $PGE_2$ by DM1 myoblasts. Human myoblasts (muscular biopsies from cDM1 foetuses) were cultured in MB-1 medium supplemented with 15% FBS and rEGF. At 70-80% confluence, cells were transferred in MB-1 medium (no FBS)+Aspirin™ (acetylsalicylic acid, Sigma Cat No. 5376) at a concentration of 0 mM or 10 mM and incubated for 48 hours. The amount of $PGE_2$ in the supernatant was measured as described above.

Effect of Aspirin™ on the differentiation of DM1 myoblasts. Human myoblasts (muscular biopsies from cDM1 foetuses) were cultured in MB-1 medium supplemented with 15% FBS and rEGF. At 70-80% confluency, cells were transferred in MB-1 medium (no FBS)+Aspirin™ at the indicated concentrations and incubated for 48 hours. Cells were then transferred in DMEM high glucose medium supplemented with 0.5% FBS, insulin and apotransferin, and in the presence of the indicated doses of Aspirin™. Cells were incubated for three days, fixed using 4% paraformaldehyde (Anachemia, Cat. No. AC-7020) and stained using 100 ng/ml DAPI (Sigma, Cat. No. D8417).

Example 2

CTG Expansion in DM1 Myoblasts

Because DM1-750 and DM1-1200 myoblasts were obtained from aborted fetuses, it was not clinically determined if they had DM1 or cDM1. The only reliable feature to diagnose the congenital form of the disease at the molecular level is to examine the proximal region of the CTG expansion that was shown to be aberrantly methylated in cDM1 (Steinbach et al., 1998, supra; Filippova et al., 2001. *Nat Genet.* 28(4): 335-43). Normal DMPK alleles generate a single 1.8 kb fragment following co-digestion by SacI and HindIII (SI/H) and mutant alleles generate a band augmented by the corresponding length of the CTG expansion. Triple digestion with SacI, SacII and HindIII (SI/SII/H) results in loss of the expansions in normal and in DM1 myoblasts (DM1-750 and DM1-1200) and generate a 1.6 kb fragment (FIG. 15). On the other hand, in cDM1, the expansion is retained in the digested fragment and generate fragments of 11.4 kb, 11.7 kb or 12.9 kb for the cells with 3200, 3300 and 3700 CTG repeats, respectively (FIG. 15). These restriction assays permit to confirm that CDM1-3200, CDM-3300 and CDM1-3700 myoblasts present a methylation pattern typical of cDM1 myoblasts. These data also indicate that DM-750 and DM-1200 are not cDM1 myoblasts.

Example 3

Alteration in the Fusion Index of Myoblasts from cDM1 Subjects

To investigate the mechanism involved in impaired myogenesis and subsequently to the defective muscle development observed in the severe congenital cDM1, myogenic differentiation of primary myoblasts isolated from cDM1 patients but also from DM1, DM2 and non-affected individual (CON) was assessed in vitro (see FIGS. 1 and 13). Fusion of cDM1 myoblasts associated with large expansion (>3000 CTG) was significantly reduced by 70-80% when compared to DM2 and CON muscle cells (FIG. 13a). A slight decrease of fusion index (25%) was also measured in DM1 cells containing 750 CTG and 1200 CTG suggesting that an additional mechanism may trigger the altered differentiation of cDM1 myoblasts.

Example 4

Alteration in the Fusion Index of Normal Myoblasts Co-Cultured with DM-3200 Myoblasts As shown in FIG. 2, the culture of normal myoblasts in the presence of DM1 myoblasts affects their capacity to fuse (compare panel (A) vs. (C), and panel (B) vs. (D)). These results indicate that a soluble factor secreted by DM1 myoblasts inhibited myogenic fusion of normal myoblasts.

Example 5

Figure 3:
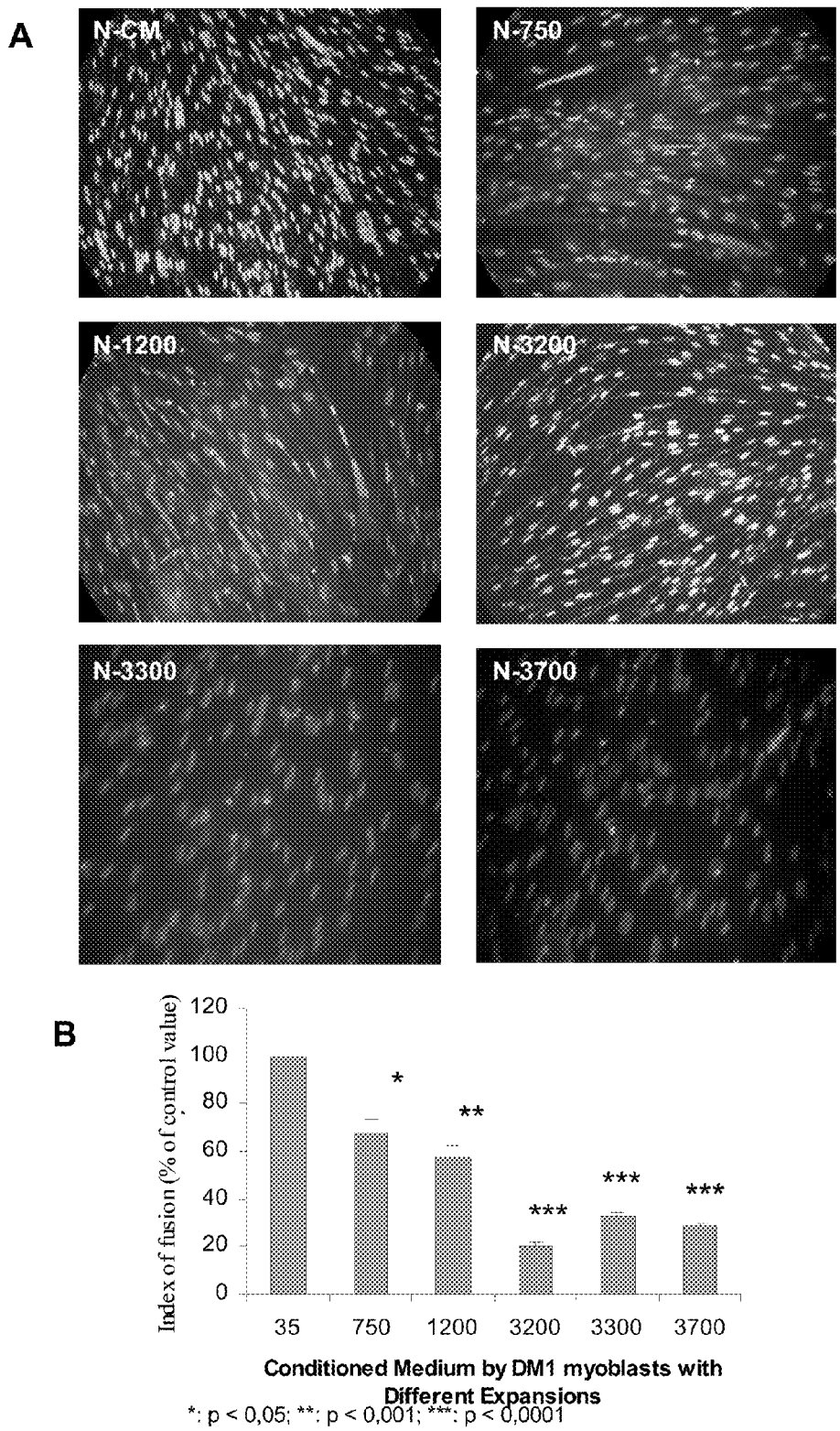
FIG. 3 shows the effect of DM1-conditioned medium on the index of fusion of normal myoblasts; (A) Control myoblasts were incubated with conditioned medium (CM) from normal (N-CM), DM1 with 750 (N-750), 1200 (N-1200) and 3200 CTG repeats (N-3200), or cDM1 with 3300 (N-3300) and 3700 (N-3700) repeats. After 4 days of differentiation, cells were fixed with 4% formaldehyde and stained with DAPI. (B) Quantitation of the fusion index. The number of nuclei in multinucleated myotubes is expressed as a percentage of the total number of nuclei. About 1000 nuclei from three independent experiments were counted.

Alteration in the Fusion Index of Normal Myoblasts Exposed to the Conditioned Medium Normal myoblasts were differentiated in conditioned medium (CM) collected from CON, DM1, DM2 and cDM1 cultures (FIGS. 3 and 13b). Only differentiated cultures incubated with CM collected from cDM1 muscle cells completely inhibit the fusion of normal myoblasts indicating that a soluble factor secreted by cDM1 cells may inhibit their differentiation (FIG. 13b). The 20-30% decrease of the fusion index of normal myoblasts incubated with CM from normal cells may be explained by the presence of proliferative components in the medium used during differentiation. The data presented in FIG. 3 show that conditioned medium (CM) generated from cDM1 cells inhibit the ability of normal myoblasts to fuse/differentiate. Furthermore, the results demonstrate that there is a relationship between the ability of CM to inhibit myoblast differentiation and the length of the CTG repeat expansion in DM1 cells used to generate the conditioned medium, suggesting that the production of the soluble factor is influenced by the extent of the CTG repeat expansion. FIG. 4 shows that conditioned medium (CM) generated from DM2 cells does not significantly affect the differentiation of normal myoblasts.

Example 6

Effect of Fractionated Conditioned Medium on the Index of Fusion

Figure 5:
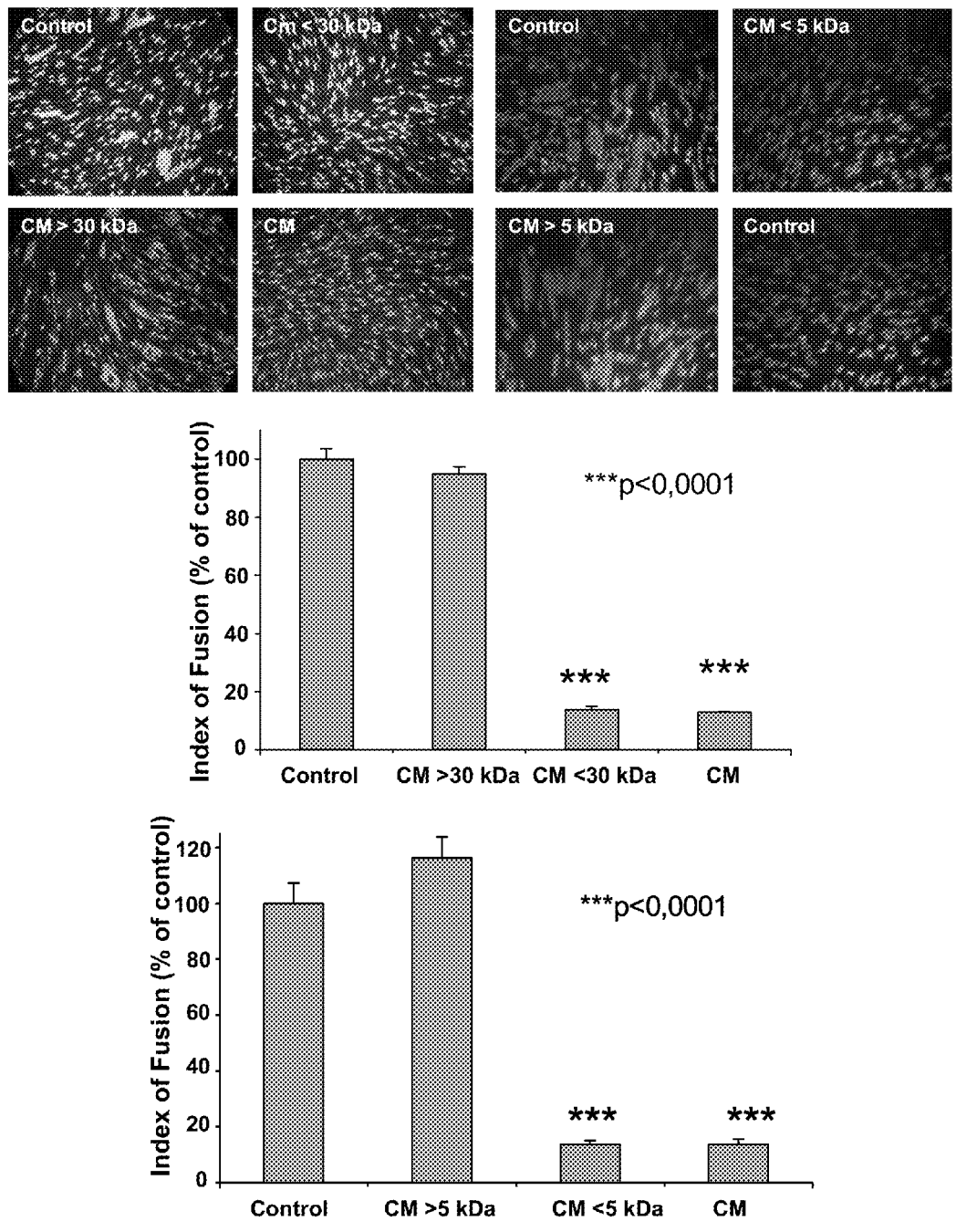
FIG. 5 shows that the factor responsible for the inhibition of the fusion of normal myoblasts has a molecular weight of less than 5 KDa. Normal myoblasts were either grown in unfractionated CM or fractionated conditioned medium (CM<30 kDa and CM>30 kDa (left) or CM<5 kDa and CM>5 kDa (right)), both generated from DM1 myoblasts with 3200 repeats after 4 days in differentiating medium. Cells were stained with DAPI. Fusion index of normal myoblasts incubated with conditioned medium containing proteins larger than 30 kDa (>30 kDa) or smaller than 30 kDa (<30 kDa) (left) or larger than 5 kDa (CM<5 kDa and CM>5 kDa (right)). One thousand (1000) nuclei were counted.

The results presented in FIG. 5 demonstrate that the soluble factor secreted by cDM1 cells that inhibits the fusion or normal myoblasts has a molecular weight of less than 5 kDa, as conditioned medium in which molecules having a molecular weight<5 kDa have been depleted by filtration (CM>5 kDa) has no significant effect on myoblast fusion (FIG. 5. lower right panel, second bar), whereas conditioned medium in which molecules having a molecular weight>5 kDa have been depleted by filtration (CM<5 kDa) still inhibits myoblast fusion to a level comparable to unfractionated conditioned medium (FIG. 5. lower right panel, third and fourth bars).

Example 7

Figure 6:
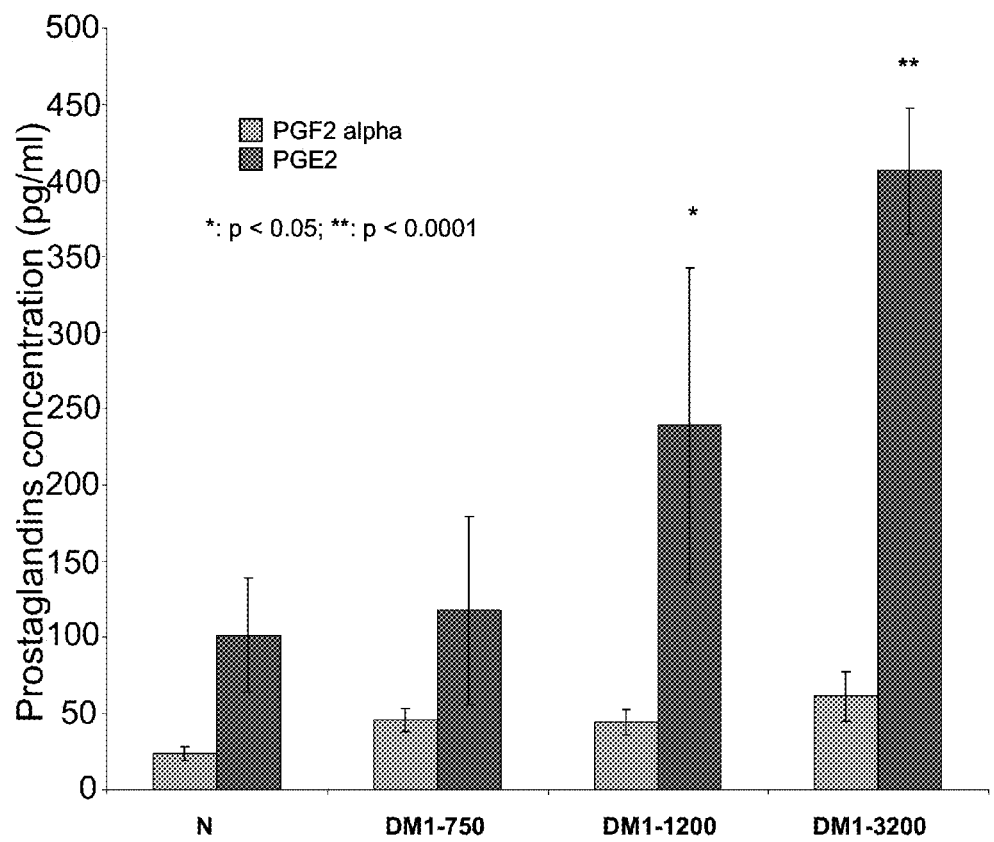
FIG. 6 shows the concentration of $PGE_2$ (dark bars) and $PGF_2$-alpha (light bars) in conditioned medium of cDM1 myoblasts. Four (4) samples of conditioned medium were analyzed per experiment (n=3)

$PGE_2$ and $PGF_2$-Alpha Concentration in Conditioned Medium from cDM1 Myoblasts There is a positive correlation between the amount of $PGE_2$ (but not $PGF_2$-alpha) produced by the DM1 myoblasts in the conditioned medium and the extent of the CTG repeat expansion (FIG. 6). Also, a 4-fold increase in the level of $PGE_2$, but not $PGF_2$-alpha, was measured in cDM1 medium when compared to DM1 or CON (FIG. 13c). This increase was correlated with a higher level of cyclooxygenase-2 (COX-2) protein, a rate-limiting enzyme involved in the prostaglandin synthesis, in cDM1 myoblasts when compared to CON cells (FIG. 13d).

Example 8

Figure 7:
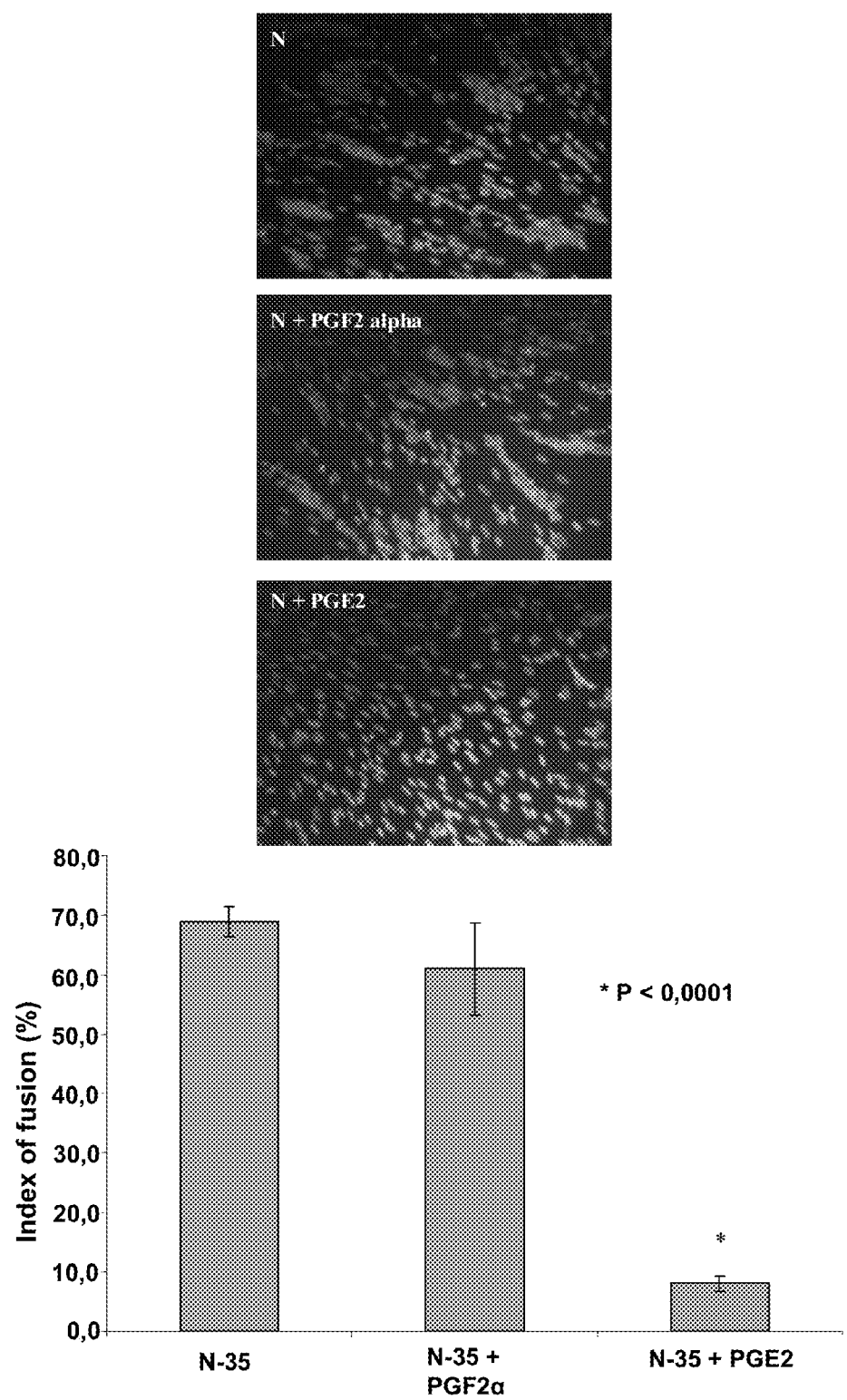
FIG. 7 shows that $PGE_2$, but not $PGF_2$-alpha, has an inhibitory effect on the fusion of normal myoblasts; Control myoblasts (N-35) were either untreated, incubated with 10 mM $PGE_2$ or 10 mM $PGF_2$-alpha. After 4 days of differentiation, cells were fixed with paraformaldehyde and stained with DAPI. For the quantitation of the fusion index, the number of nuclei in multinucleated myotubes is expressed as a percentage of the total number of nuclei. About 1000 nuclei from three independent experiments were counted.
Figure 17:
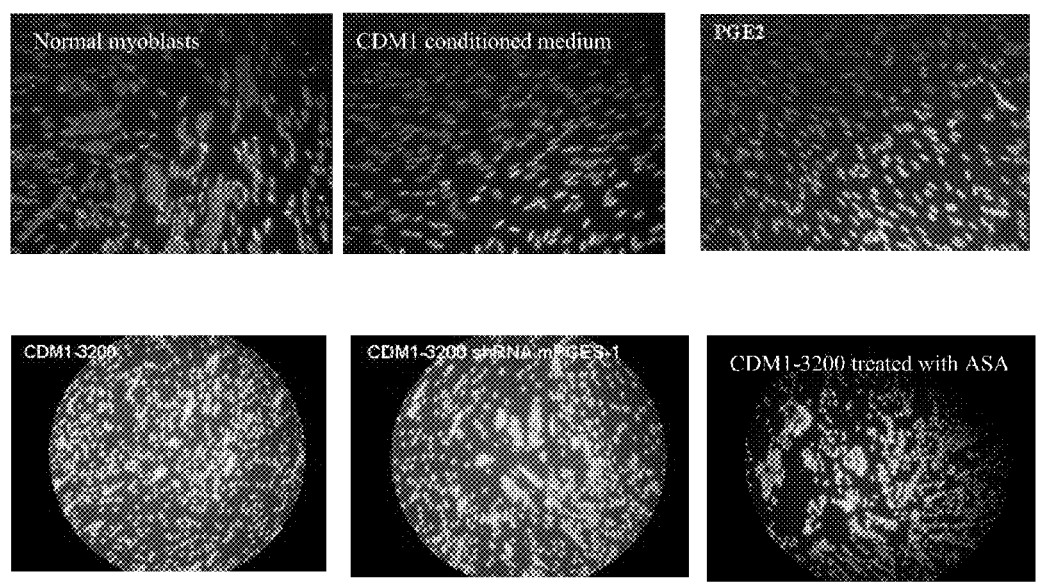
FIG. 17 shows in vitro studies addressing the involvement of prostaglandin $E_2$ in the fusion of myoblasts. 80% of normal cultured myoblasts fused after 4 days in differentiating medium (upper left panel). CDM1-3200 myoblasts did not fuse in the same culture conditions (lower left panel). Culture of normal myoblasts in a medium conditioned by CDM1 cells completely abolished their fusion (upper middle panel) as well as treatment of these cells with 1 μM of $PGE_2$ (upper right panel). Treatment of CDM1 myoblasts with shRNA mPGES-1 (lower middle panel) or 2 mM ASA (lower right panel) restore their ability to fuse.

Assessment of the Fusion Index of Normal Myoblasts Exposed to $PGE_2$ or $PG F_2$-Alpha As shown in FIGS. 7, 14a and 17, incubation of normal myoblasts with different amounts of $PGE_2$ inhibits their myogenic differentiation with maximal effect occurring at a concentration of 1 µM. In contrast, $PGF_2$-alpha has no significant effect on myogenic differentiation (FIG. 7).

Example 9

COX-2 Expression in DM1 Cells, cDM1 and Adult DM1 Muscle Biopsies

Data presented in FIG. 8 demonstrate that (i) there appears to be a correlation between the ability of myoblasts to fuse and the expression of COX-2 protein (FIG. 8a); DM1-1200 and DM1-3200 myoblasts expresses higher levels of COX-2 and have a lower index of fusion (see FIG. 1) as compared to DM1-750 myoblasts, and (ii) that the expression of COX-2 is restricted to the fetal form of DM1 (cDM1) (FIG. 8b). COX-2 expression was specifically increased in muscle cells of cDM1 patients when compared to muscle cells of DM1 or CON subjects (FIG. 13e), indicating that the biosynthetic cascade/pathway involved in the production of $PGE_2$ is upregulated in muscle cells of cDM1 subjects.

Example 10

Partial Restoration of the Fusion of cDM1 After Inhibition of mPGES-1 Gene Expression by RNA Interference To assess the inhibitory effect of $PGE_2$ secreted by cDM1 cells, the microsomal prostaglandin E synthase (mPGES-1), an enzyme involved in COX-2 dependent $PGE_2$ synthesis (Murakami and Kudo, 2004. *Prog Lipid Res* 43: 3-35) was silenced using RNA interference. FIG. 9a shows that the vector expressing a shRNA directed against mPGES-1 mRNA significantly decreases the expression of mPGES-1 mRNA in DM1-3200 myoblasts. A 4-fold decrease in PGE2 levels was measured in the medium of cDM1-shRNA-mPGES-1 cells (FIG. 14b). This decrease in mPGES-1 expression significantly increases (by about 2-fold) the myogenic differentiation of cDM1 cells (FIGS. 9b, 9c, 14d and 17), indicating that mPGES-1 activity is involved in $PGE_2$ production by cDM1 cells.

Example 11

Figure 10:
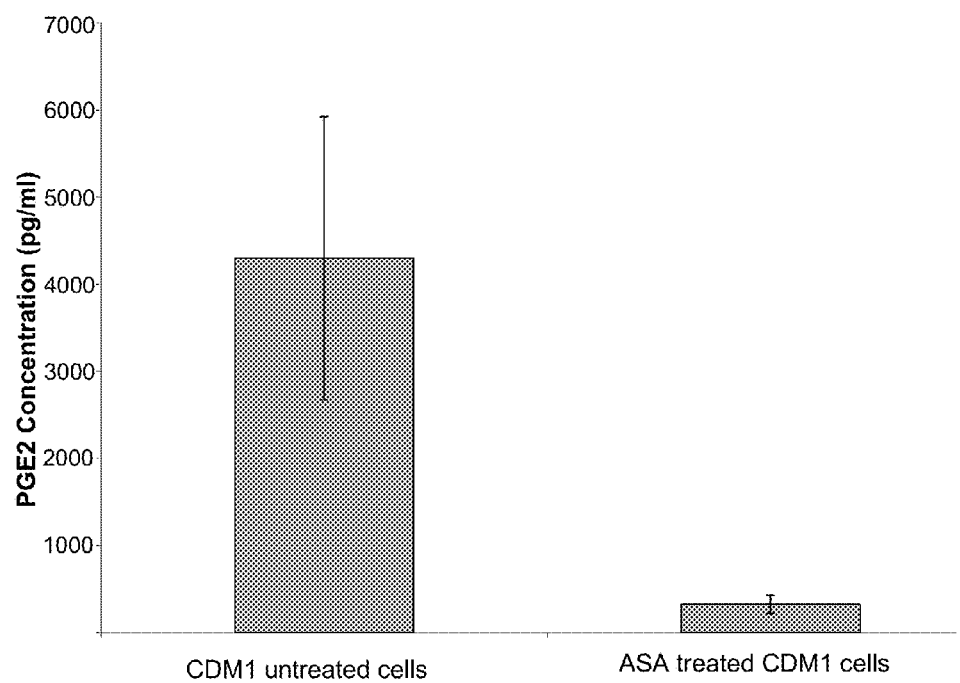
FIG. 10 shows the effect of acetylsalicyclic acid (ASA, Aspirin™) on the production of $PGE_2$ by cDM1 myoblasts. Left bar=untreated cDM1 myoblasts; right bar=cDM1 cells treated with 10 mM Aspirin™.
Figure 11:
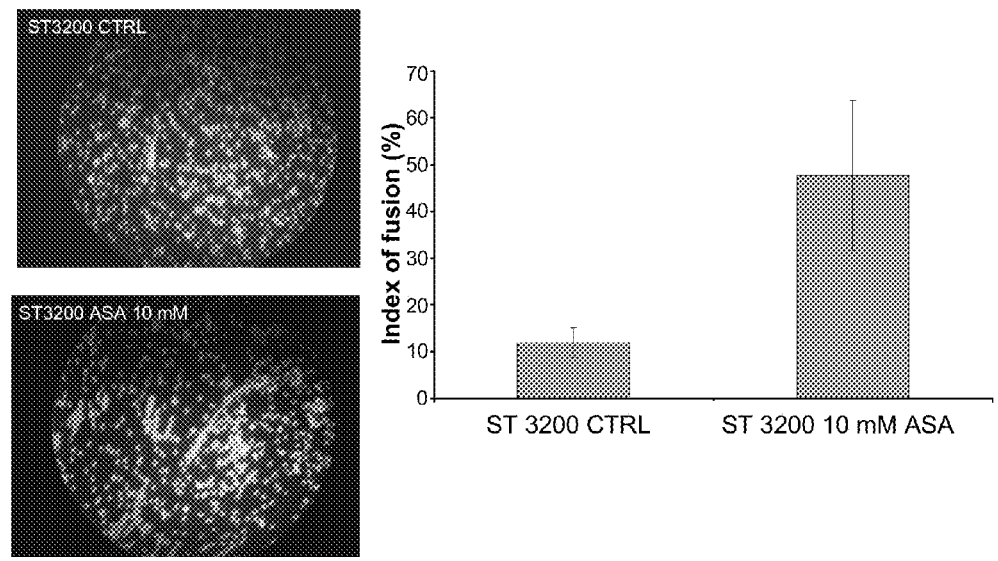
FIG. 11 shows the effect of acetylsalicyclic acid (ASA) on the differentiation of cDM1 myoblasts. Control myoblasts (N-35) were incubated with 10 mM acetylsalicyclic acid (ASA). After 4 days of differentiation, cells were fixed with formaldehyde and stained with DAPI. For the quantitation of the fusion index, the number of nuclei in multinucleated myotubes is expressed as a percentage of the total number of nuclei. About 1000 nuclei from three independent experiments were counted. In the graph: left bar=untreated cDM1 myoblasts; right bar=cDM1 cells treated with 10 mM ASA.

Effect of Acetylsalicylic Acid (Aspirin™) on $PGE_2$ Secretion and Myogenic Differentiation of cDM1 Cells Different biosynthetic routes are involved in $PGE_2$ production. In fact, $PGE_2$ can be catalyzed by at least three different PGE synthases from PGH$_2$ that is formed from oxygenation of arachidonic acid by COX-1 or COX-2 enzymes (Murakami and Kudo, 2004, supra). Since both cyclooxygenase are able to catalyze the first step of prostaglandin production, cDM1 cell cultures were treated with increasing concentration of acetylsalycilic acid (ASA), an inhibitor of both COX-1 and COX-2 enzymes (Vane and Botting, 2003. *Thromb Res.* 110: 255-258). In the presence of ASA, PGE$_2$ level was decreased in a dose-dependent manner with maximal decreased (90%) observed at a concentration of 2 mM (FIGS. 10 and 14*c*), and a concomitant increase by about 4-fold of the fusion index was measured in these cultures (FIGS. 11, 14*d* and 17). Thus, exogenous addition of ASA restores myogenic differentiation of cDM1 muscle cells and these cDM1-treated cells reach a comparable fusion index that non-congenital DM1 myoblasts (~50% vs. ~70-80%, respectively).

Although the present invention has been described hereinabove by way of specific embodiments thereof, it can be modified, without departing from the spirit and nature of the subject invention as defined in the appended claims.

What is claimed is:

1. A method for determining whether a test compound is useful for increasing myoblast differentiation in a subject suffering from cDM1, said method comprising determining the level and/or activity of (i) $PGE_2$, (ii) mPGES-1, or (iii) both (i) and (ii), in a myoblast comprising (i) $PGE_2$, (ii) mPGES-1, (iii) both (i) and (ii), and/or $PGE_2$ biosynthetic activity; wherein a decrease in the level and/or activity in the presence relative to the absence of said test compound is indicative that said test compound is useful for increasing myoblast differentiation in the subject suffering from cDM1, and wherein said test compound does not significantly modulate $PGF_2$-alpha levels and/or activity.

2. A method for determining whether a test compound is useful for increasing myoblast differentiation in a subject suffering from cDM1, said method comprising:
  (a) contacting a myoblast sample from the subject suffering from cDM1 with said test compound; and
  (b) determining the level and/or activity of (i) $PGE_2$, (ii) mPGES-1, or (iii) both (i) and (ii); wherein a decrease in the level and/or activity in the presence relative to in the absence of said test compound is indicative that said test compound is useful for increasing myoblast differentiation in the subject suffering from cDM1, and wherein said test compound does not significantly modulate $PGF_2$-alpha levels and/or activity.

3. A method for determining whether a test compound is useful for increasing myoblast differentiation in a subject suffering from cDM1, said method comprising assaying the level and/or activity of (i) $PGE_2$, (ii) mPGES-1, or (iii) both (i) and (ii), in the presence versus in the absence of said test compound, wherein a decrease in the level and/or activity in the presence relative to the absence of said test compound is indicative that said test compound is useful for increasing myoblast differentiation in the subject suffering from cDM1, and wherein said test compound does not significantly modulate $PGF_2$-alpha levels and/or activity.

4. The method of claim 3, wherein said assaying comprises contacting said test compound with a cell comprising (i) $PGE_2$, (ii) mPGES-1, or (iii) both (i) and (ii).

5. The method of claim 3, wherein said assaying comprises contacting said test compound with mPGES-1.

6. The method of claim 1, further comprising:
  contacting a myoblast sample from the subject suffering from cDM1 with said test compound;
  culturing said myoblast under conditions suitable for myoblast differentiation; and
  determining the level of differentiation of said myoblast;
  wherein an increase in the level of differentiation of said myoblast in the presence relative to the absence of said test compound is indicative that said test compound is useful for increasing myoblast differentiation in the subject suffering from cDM1.

7. The method of claim 6, wherein said level of differentiation is determined by measuring the index of fusion of said myoblast after said culturing.

8. The method of claim 2, further comprising:
  contacting the myoblast sample from the subject suffering from cDM1 with said test compound;
  culturing said myoblast under conditions suitable for myoblast differentiation; and
  determining the level of differentiation of said myoblast;
  wherein an increase in the level of differentiation of said myoblast in the presence relative to the absence of said test compound is indicative that said test compound is useful for increasing myoblast differentiation in the subject suffering from cDM1.

* * * * *

```
                        SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tgcattcttt gcccagcact                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
aaaggcgcag tttacgctgt                                              20

<210> SEQ ID NO 3
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 3
aaagggagac tctatttaag attagtgaag ccacagatgt aatcttaaat agagtctccc   60
ttc                                                                63

<210> SEQ ID NO 4
<211> LENGTH: 97
<212> TYPE: DNA
<213> ORGANISM: Artificial Sequence
<220> FEATURE:
<223> OTHER INFORMATION: Synthetic oligonucleotide

<400> SEQUENCE: 4
tgctgttgac agtgagcgaa agggagactc tatttaagat tagtgaagcc acagatgtaa   60
tcttaaatag agtctccctt ctgcctactg cctcgga                           97

<210> SEQ ID NO 5
<211> LENGTH: 1805
<212> TYPE: DNA
<213> ORGANISM: Homo sapiens
<220> FEATURE:
<221> NAME/KEY: CDS
<222> LOCATION: (54)..(512)
```

<400> SEQUENCE: 5

```
gctgctcctc tgtcgagctg atcacaccca cagttgagct gcgctggcca gag atg      56
                                                            Met
                                                            1 cct gcc cac agc ctg gtg atg agc agc ccg gcc ctc ccg gcc ttc ctg    104
Pro Ala His Ser Leu Val Met Ser Ser Pro Ala Leu Pro Ala Phe Leu
        5                  10                  15 ctc tgc agc acg ctg ctg gtc atc aag atg tac gtg gtg gcc atc atc    152
Leu Cys Ser Thr Leu Leu Val Ile Lys Met Tyr Val Val Ala Ile Ile
         20                  25                  30 acg ggc caa gtg agg ctg cgg aag aag gcc ttt gcc aac ccc gag gat    200
Thr Gly Gln Val Arg Leu Arg Lys Lys Ala Phe Ala Asn Pro Glu Asp
         35                  40                  45 gcc ctg aga cac gga ggc ccc cag tat tgc agg agc gac ccc gac gtg    248
Ala Leu Arg His Gly Gly Pro Gln Tyr Cys Arg Ser Asp Pro Asp Val
50                  55                  60                  65 gaa cgc tgc ctc agg gcc cac cgg aac gac atg gag acc atc tac ccc    296
Glu Arg Cys Leu Arg Ala His Arg Asn Asp Met Glu Thr Ile Tyr Pro
                 70                  75                  80 ttc ctt ttc ctg ggc ttc gtc tac tcc ttt ctg ggt cct aac cct ttt    344
Phe Leu Phe Leu Gly Phe Val Tyr Ser Phe Leu Gly Pro Asn Pro Phe
             85                  90                  95 gtc gcc tgg atg cac ttc ctg gtc ttc ctc gtg ggc cgt gtg gca cac    392
Val Ala Trp Met His Phe Leu Val Phe Leu Val Gly Arg Val Ala His
        100                 105                 110 acc gtg gcc tac ctg ggg aag ctg cgg gca ccc atc cgc tcc gtg acc    440
Thr Val Ala Tyr Leu Gly Lys Leu Arg Ala Pro Ile Arg Ser Val Thr
        115                 120                 125 tac acc ctg gcc cag ctc ccc tgc gcc tcc atg gct ctg cag atc ctc    488
Tyr Thr Leu Ala Gln Leu Pro Cys Ala Ser Met Ala Leu Gln Ile Leu
130                 135                 140                 145 tgg gaa gcg gcc cgc cac ctg tga ccagcagctg atgcctcctt ggccaccaga   542
Trp Glu Ala Ala Arg His Leu
                150 ccatgggcca agagccgccg tggctatacc tggggacttg atgttccttc cagattgtgg   602
tgggccctga gtcctggttt cctggcagcc tgctgcgcgt gtgggtctct gggcacagtg   662
ggcctgtgtg tgtgcccgtg tgtgtgtatg tgtgtgtgta tgtttcttag ccccttggat   722
tcctgcacga agtggctgat gggaaccatt tcaagacaga ttgtgaagat tgatagaaaa   782
tccttcagct aaagtaacag agcatcaaaa acatcactcc ctctccctcc ctaacagtga   842
aaagagagaa gggagactct atttaagatt cccaaaccta atgatcatct gaatcccggg   902
ctaagaatgc agacttttca gactgacccc agaaattctg gcccagccaa tctagaggca   962
agcctggcca tctgtatttt ttttttttcca agacagagtc ttgctctgtt gcccaagctg  1022
gagtgaagtg gtacaatctg gctcactgca gcctccgcct cccgggttca gcgattctc   1082
ccgcctcagc ctcctgagta gctgggatta caggcgcgta tcaccatacc cagctaattt  1142
ttgtattttt agtagagacg ggttcaccat gttgcccagg agggtctcga actcctggcc  1202
tcaagtgatc caccggcctc ggcctcccaa agtgctggga tgacaggcat gaatcactgt  1262
gctcagccac catctggagt tttaaaaggc tccatgtga gtccctgtga tggcaggcc    1322
aggggacccc tgccagttct ctgtggaagc aaggctgggg tcttgggttc ctgtatggtg  1382
gaagctgggt gagccaagga cagggctggc tcctctgccc ccgctgacgc ttcccttgcc  1442
gttggctttg gatgtctttg ctgcagtctt ctctctggct caggtgtggg tgggaggggc  1502
ccacaggaag ctcagccttc tcctcccaag gtttgagtcc ctccaaaggg cagtgggtgg  1562
```

-continued

```
aggaccggga gctttgggtg accagccact caaaggaact ttctggtccc ttcagtatct      1622
tcaaggtttg gaaactgcaa atgtcccctt gatggggaat ccgtgtgtgt gtgtgtgtgt      1682
gtgtgtgtgt gtgtgtgtgt gtgtgttttc tcctagaccc gtgacctgag atgtgtgatt      1742
tttagtcatt aaatggaagt gtctgccagc tgggcccagc acctaaaaaa aaaaaaaaaa      1802
aaa                                                                    1805

<210> SEQ ID NO 6
<211> LENGTH: 152
<212> TYPE: PRT
<213> ORGANISM: Homo sapiens

<400> SEQUENCE: 6

Met Pro Ala His Ser Leu Val Met Ser Ser Pro Ala Leu Pro Ala Phe
1               5                   10                  15

Leu Leu Cys Ser Thr Leu Leu Val Ile Lys Met Tyr Val Val Ala Ile
            20                  25                  30

Ile Thr Gly Gln Val Arg Leu Arg Lys Lys Ala Phe Ala Asn Pro Glu
        35                  40                  45

Asp Ala Leu Arg His Gly Gly Pro Gln Tyr Cys Arg Ser Asp Pro Asp
    50                  55                  60

Val Glu Arg Cys Leu Arg Ala His Arg Asn Asp Met Glu Thr Ile Tyr
65                  70                  75                  80

Pro Phe Leu Phe Leu Gly Phe Val Tyr Ser Phe Leu Gly Pro Asn Pro
                85                  90                  95

Phe Val Ala Trp Met His Phe Leu Val Phe Leu Val Gly Arg Val Ala
            100                 105                 110

His Thr Val Ala Tyr Leu Gly Lys Leu Arg Ala Pro Ile Arg Ser Val
        115                 120                 125

Thr Tyr Thr Leu Ala Gln Leu Pro Cys Ala Ser Met Ala Leu Gln Ile
    130                 135                 140

Leu Trp Glu Ala Ala Arg His Leu
145                 150

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
gaagaaggcc tttgccaac                                                   19

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gggttaggac ccagaaagga                                                  20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide
```

-continued

```
<400> SEQUENCE: 9
gcgggaaatc gtgcgtgaca tt                                              22

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
gatggagttg aaggtagttt cgtg                                            24

<210> SEQ ID NO 11
<211> LENGTH: 4465
<212> TYPE: DNA
<213> ORGANISM: Homo sapiens
<220> FEATURE:
<221> NAME/KEY: CDS
<222> LOCATION: (135)..(1949)

<400> SEQUENCE: 11
caattgtcat acgacttgca gtgagcgtca ggagcacgtc caggaactcc tcagcagcgc     60
ctccttcagc tccacagcca gacgccctca gacagcaaag cctaccccg  cgccgcgccc    120 tgcccgccgc tcgg atg ctc gcc cgc gcc ctg ctg ctg tgc gcg gtc ctg     170
              Met Leu Ala Arg Ala Leu Leu Leu Cys Ala Val Leu
                1               5                   10 gcg ctc agc cat aca gca aat cct tgc tgt tcc cac cca tgt caa aac     218
Ala Leu Ser His Thr Ala Asn Pro Cys Cys Ser His Pro Cys Gln Asn
         15                  20                  25 cga ggt gta tgt atg agt gtg gga ttt gac cag tat aag tgc gat tgt     266
Arg Gly Val Cys Met Ser Val Gly Phe Asp Gln Tyr Lys Cys Asp Cys
 30                  35                  40 acc cgg aca gga ttc tat gga gaa aac tgc tca aca ccg gaa ttt ttg     314
Thr Arg Thr Gly Phe Tyr Gly Glu Asn Cys Ser Thr Pro Glu Phe Leu
 45                  50                  55                  60 aca aga ata aaa tta ttt ctg aaa ccc act cca aac aca gtg cac tac     362
Thr Arg Ile Lys Leu Phe Leu Lys Pro Thr Pro Asn Thr Val His Tyr
                 65                  70                  75 ata ctt acc cac ttc aag gga ttt tgg aac gtt gtg aat aac att ccc     410
Ile Leu Thr His Phe Lys Gly Phe Trp Asn Val Val Asn Asn Ile Pro
             80                  85                  90 ttc ctt cga aat gca att atg agt tat gtc ttg aca tcc aga tca cat     458
Phe Leu Arg Asn Ala Ile Met Ser Tyr Val Leu Thr Ser Arg Ser His
         95                 100                 105 ttg att gac agt cca cca act tac aat gct gac tat ggc tac aaa agc     506
Leu Ile Asp Ser Pro Pro Thr Tyr Asn Ala Asp Tyr Gly Tyr Lys Ser
    110                 115                 120 tgg gaa gcc ttc tct aac ctc tcc tat tat act aga gcc ctt cct cct     554
Trp Glu Ala Phe Ser Asn Leu Ser Tyr Tyr Thr Arg Ala Leu Pro Pro
125                 130                 135                 140 gtg cct gat gat tgc ccg act ccc ttg ggt gtc aaa ggt aaa aag cag     602
Val Pro Asp Asp Cys Pro Thr Pro Leu Gly Val Lys Gly Lys Lys Gln
                145                 150                 155 ctt cct gat tca aat gag att gtg gaa aaa ttg ctt cta aga aga aag     650
Leu Pro Asp Ser Asn Glu Ile Val Glu Lys Leu Leu Leu Arg Arg Lys
            160                 165                 170 ttc atc cct gat ccc cag ggc tca aac atg atg ttt gca ttc ttt gcc     698
Phe Ile Pro Asp Pro Gln Gly Ser Asn Met Met Phe Ala Phe Phe Ala
        175                 180                 185
```

```
cag cac ttc acg cat cag ttt ttc aag aca gat cat aag cga ggg cca      746
Gln His Phe Thr His Gln Phe Phe Lys Thr Asp His Lys Arg Gly Pro
    190                 195                 200 gct ttc acc aac ggg ctg ggc cat ggg gtg gac tta aat cat att tac      794
Ala Phe Thr Asn Gly Leu Gly His Gly Val Asp Leu Asn His Ile Tyr
205                 210                 215                 220 ggt gaa act ctg gct aga cag cgt aaa ctg cgc ctt ttc aag gat gga      842
Gly Glu Thr Leu Ala Arg Gln Arg Lys Leu Arg Leu Phe Lys Asp Gly
                225                 230                 235 aaa atg aaa tat cag ata att gat gga gag atg tat cct ccc aca gtc      890
Lys Met Lys Tyr Gln Ile Ile Asp Gly Glu Met Tyr Pro Pro Thr Val
240                 245                 250 aaa gat act cag gca gag atg atc tac cct cct caa gtc cct gag cat      938
Lys Asp Thr Gln Ala Glu Met Ile Tyr Pro Pro Gln Val Pro Glu His
            255                 260                 265 cta cgg ttt gct gtg ggg cag gag gtc ttt ggt ctg gtg cct ggt ctg      986
Leu Arg Phe Ala Val Gly Gln Glu Val Phe Gly Leu Val Pro Gly Leu
    270                 275                 280 atg atg tat gcc aca atc tgg ctg cgg gaa cac aac aga gta tgc gat     1034
Met Met Tyr Ala Thr Ile Trp Leu Arg Glu His Asn Arg Val Cys Asp
285                 290                 295                 300 gtg ctt aaa cag gag cat cct gaa tgg ggt gat gag cag ttg ttc cag     1082
Val Leu Lys Gln Glu His Pro Glu Trp Gly Asp Glu Gln Leu Phe Gln
                305                 310                 315 aca agc agg cta ata ctg ata gga gag act att aag att gtg att gaa     1130
Thr Ser Arg Leu Ile Leu Ile Gly Glu Thr Ile Lys Ile Val Ile Glu
320                 325                 330 gat tat gtg caa cac ttg agt ggc tat cac ttc aaa ctg aaa ttt gac     1178
Asp Tyr Val Gln His Leu Ser Gly Tyr His Phe Lys Leu Lys Phe Asp
            335                 340                 345 cca gaa cta ctt ttc aac aaa caa ttc cag tac caa aat cgt att gct     1226
Pro Glu Leu Leu Phe Asn Lys Gln Phe Gln Tyr Gln Asn Arg Ile Ala
    350                 355                 360 gct gaa ttt aac acc ctc tat cac tgg cat ccc ctt ctg cct gac acc     1274
Ala Glu Phe Asn Thr Leu Tyr His Trp His Pro Leu Leu Pro Asp Thr
365                 370                 375                 380 ttt caa att cat gac cag aaa tac aac tat caa cag ttt atc tac aac     1322
Phe Gln Ile His Asp Gln Lys Tyr Asn Tyr Gln Gln Phe Ile Tyr Asn
                385                 390                 395 aac tct ata ttg ctg gaa cat gga att acc cag ttt gtt gaa tca ttc     1370
Asn Ser Ile Leu Leu Glu His Gly Ile Thr Gln Phe Val Glu Ser Phe
                400                 405                 410 acc agg caa att gct ggc agg gtt gct ggt ggt agg aat gtt cca ccc     1418
Thr Arg Gln Ile Ala Gly Arg Val Ala Gly Gly Arg Asn Val Pro Pro
            415                 420                 425 gca gta cag aaa gta tca cag gct tcc att gac cag agc agg cag atg     1466
Ala Val Gln Lys Val Ser Gln Ala Ser Ile Asp Gln Ser Arg Gln Met
    430                 435                 440 aaa tac cag tct ttt aat gag tac cgc aaa cgc ttt atg ctg aag ccc     1514
Lys Tyr Gln Ser Phe Asn Glu Tyr Arg Lys Arg Phe Met Leu Lys Pro
445                 450                 455                 460 tat gaa tca ttt gaa gaa ctt aca gga gaa aag gaa atg tct gca gag     1562
Tyr Glu Ser Phe Glu Glu Leu Thr Gly Glu Lys Glu Met Ser Ala Glu
                465                 470                 475 ttg gaa gca ctc tat ggt gac atc gat gct gtg gag ctg tat cct gcc     1610
Leu Glu Ala Leu Tyr Gly Asp Ile Asp Ala Val Glu Leu Tyr Pro Ala
            480                 485                 490 ctt ctg gta gaa aag cct cgg cca gat gcc atc ttt ggt gaa acc atg     1658
Leu Leu Val Glu Lys Pro Arg Pro Asp Ala Ile Phe Gly Glu Thr Met
    495                 500                 505
```

```
gta gaa gtt gga gca cca ttc tcc ttg aaa gga ctt atg ggt aat gtt    1706
Val Glu Val Gly Ala Pro Phe Ser Leu Lys Gly Leu Met Gly Asn Val
    510                 515                 520 ata tgt tct cct gcc tac tgg aag cca agc act ttt ggt gga gaa gtg    1754
Ile Cys Ser Pro Ala Tyr Trp Lys Pro Ser Thr Phe Gly Gly Glu Val
525                 530                 535                 540 ggt ttt caa atc atc aac act gcc tca att cag tct ctc atc tgc aat    1802
Gly Phe Gln Ile Ile Asn Thr Ala Ser Ile Gln Ser Leu Ile Cys Asn
                545                 550                 555 aac gtg aag ggc tgt ccc ttt act tca ttc agt gtt cca gat cca gag    1850
Asn Val Lys Gly Cys Pro Phe Thr Ser Phe Ser Val Pro Asp Pro Glu
            560                 565                 570 ctc att aaa aca gtc acc atc aat gca agt tct tcc cgc tcc gga cta    1898
Leu Ile Lys Thr Val Thr Ile Asn Ala Ser Ser Ser Arg Ser Gly Leu
        575                 580                 585 gat gat atc aat ccc aca gta cta cta aaa gaa cgt tcg act gaa ctg    1946
Asp Asp Ile Asn Pro Thr Val Leu Leu Lys Glu Arg Ser Thr Glu Leu
    590                 595                 600 tag aagtctaatg atcatattta tttatttata tgaaccatgt ctattaattt     1999
aattatttaa taatatttat attaaactcc ttatgttact taacatcttc tgtaacagaa     2059
gtcagtactc ctgttgcgga gaaaggagtc atacttgtga agacttttat gtcactactc     2119
taaagatttt gctgttgctg ttaagtttgg aaaacagttt ttattctgtt ttataaacca     2179
gagagaaatg agttttgacg tcttttttact tgaatttcaa cttatattat aagaacgaaa     2239
gtaaagatgt ttgaatactt aaacactatc acaagatggc aaaatgctga agttttttac     2299
actgtcgatg tttccaatgc atcttccatg atgcattaga agtaactaat gtttgaaatt     2359
ttaaagtact tttggttatt tttctgtcat caaacaaaaa caggtatcag tgcattatta     2419
aatgaatatt taaattagac attaccagta atttcatgtc tacttttttaa aatcagcaat     2479
gaaacaataa tttgaaattt ctaaattcat agggtagaat cacctgtaaa agcttgtttg     2539
atttcttaaa gttattaaac ttgtacatat accaaaaaga agctgtcttg gatttaaatc     2599
tgtaaaatca gatgaaattt tactacaatt gcttgttaaa atattttata agtgatgttc     2659
cttttttcacc aagagtataa acctttttag tgtgactgtt aaaacttcct tttaaatcaa     2719
aatgccaaat ttattaaggt ggtggagcca ctgcagtgtt atctcaaaat aagaatattt     2779
tgttgagata ttccagaatt tgtttatatg gctggtaaca tgtaaaatct atatcagcaa     2839
aagggtctac ctttaaaata agcaataaca aagaagaaaa ccaaattatt gttcaaattt     2899
aggtttaaac ttttgaagca aacttttttt tatccttgtg cactgcaggc ctggtactca     2959
gattttgcta tgaggttaat gaagtaccaa gctgtgcttg aataacgata tgttttctca     3019
gattttctgt tgtacagttt aatttagcag tccatatcac attgcaaaag tagcaatgac     3079
ctcataaaat acctcttcaa aatgcttaaa ttcatttcac acattaattt tatctcagtc     3139
ttgaagccaa ttcagtaggt gcattggaat caagcctggc tacctgcatg ctgttccttt     3199
tcttttcttc ttttagccat tttgctaaga gacacagtct tctcatcact tcgtttctcc     3259
tattttgttt tactagtttt aagatcagag ttcactttct ttggactctg cctatatttt     3319
cttacctgaa cttttgcaag ttttcaggta aacctcagct caggactgct atttagctcc     3379
tcttaagaag attaaaagag aaaaaaaaag gccctttaa aaatagtata cacttatttt     3439
aagtgaaaag cagagaattt tatttatagc taatttagc tatctgtaac caagatggat     3499
gcaaagaggc tagtgcctca gagagaactg tacggggttt gtgactggaa aaagttacgt     3559
tcccattcta attaatgccc tttcttattt aaaaacaaaa ccaaatgata tctaagtagt     3619
```

-continued

```
tctcagcaat aataataatg acgataatac ttcttttcca catctcattg tcactgacat    3679
ttaatggtac tgtatattac ttaatttatt gaagattatt atttatgtct tattaggaca    3739
ctatggttat aaactgtgtt taagcctaca atcattgatt ttttttttgtt atgtcacaat   3799
cagtatattt tctttggggt tacctctctg aatattatgt aaacaatcca agaaatgat    3859
tgtattaaga tttgtgaata aattttttaga aatctgattg gcatattgag atatttaagg  3919
ttgaatgttt gtccttagga taggcctatg tgctagccca caaagaatat tgtctcatta   3979
gcctgaatgt gccataagac tgaccttta aaatgttttg agggatctgt ggatgcttcg    4039
ttaatttgtt cagccacaat ttattgagaa aatattctgt gtcaagcact gtgggtttta   4099
atatttttaa atcaaacgct gattacagat aatagtattt atataaataa ttgaaaaaaa   4159
ttttcttttg ggaagaggga gaaatgaaa taaatatcat taaagataac tcaggagaat    4219
cttctttaca attttacgtt tagaatgttt aaggttaaga aagaaatagt caatatgctt    4279
gtataaaaca ctgttcactg tttttttttaa aaaaaaact tgatttgtta ttaacattga   4339
tctgctgaca aaacctggga atttgggttg tgtatgcgaa tgtttcagtg cctcagacaa    4399
atgtgtattt aacttatgta aaagataagt ctggaaataa atgtctgttt atttttgtac    4459
tattta                                                              4465
```

<210> SEQ ID NO 12
<211> LENGTH: 604
<212> TYPE: PRT
<213> ORGANISM: Homo sapiens

<400> SEQUENCE: 12

```
Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205
```

-continued

```
Gly Leu Gly His Gly Val Asp Leu Asn His Ile Tyr Gly Glu Thr Leu
            210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
                260                 265                 270

Val Gly Gln Glu Val Phe Gly Leu Val Pro Gly Leu Met Met Tyr Ala
                275                 280                 285

Thr Ile Trp Leu Arg Glu His Asn Arg Val Cys Asp Val Leu Lys Gln
            290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Lys Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile His
            370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
            435                 440                 445

Phe Asn Glu Tyr Arg Lys Arg Phe Met Leu Lys Pro Tyr Glu Ser Phe
            450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
            515                 520                 525

Ala Tyr Trp Lys Pro Ser Thr Phe Gly Gly Glu Val Gly Phe Gln Ile
            530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
                580                 585                 590

Pro Thr Val Leu Leu Lys Glu Arg Ser Thr Glu Leu
            595                 600
```